(12) United States Patent
Debon et al.

(10) Patent No.: US 8,413,481 B2
(45) Date of Patent: Apr. 9, 2013

(54) METHODS FOR ASSESSING MOUTHFEEL ATTRIBUTES OF FOODS USING A TRIBOLOGY DEVICE

(75) Inventors: Stéphane Jules Jérôme Debon, Brussels (FR); Brian Guthrie, Chanhassen, MN (US); Jozef Guido Roza Vanhemelrijck, Meise (BE); Stefan K. Baier, Plymouth, MN (US); Tim Lindgren, Crystal, MN (US)

(73) Assignee: Cargill, Incorporated, Wayzata, MN (US)

( * ) Notice: Subject to any disclaimer, the term of this patent is extended or adjusted under 35 U.S.C. 154(b) by 0 days.

(21) Appl. No.: 12/663,119

(22) PCT Filed: Jun. 4, 2008

(86) PCT No.: PCT/EP2008/004446
§ 371 (c)(1), (2), (4) Date: May 24, 2010

(87) PCT Pub. No.: WO2008/148538
PCT Pub. Date: Dec. 11, 2008

(65) Prior Publication Data
US 2010/0223977 A1  Sep. 9, 2010

(30) Foreign Application Priority Data
Jun. 5, 2007 (EP) .................................. 07011060

(51) Int. Cl.
*G01N 3/56* (2006.01)
*G01N 19/02* (2006.01)

(52) U.S. Cl. .................. 73/9; 426/231; 73/760; 73/788
(58) Field of Classification Search ............. 73/9, 54.01, 73/54.33, 54.35, 54.37
See application file for complete search history.

(56) References Cited

U.S. PATENT DOCUMENTS

| | | | |
|---|---|---|---|
| 5,886,268 A | 3/1999 | Larsson | |
| 6,240,770 B1 | 6/2001 | Raffer | |
| 6,499,336 B1 | 12/2002 | Raffer | |
| 6,571,610 B1 | 6/2003 | Raffer | |
| 2006/0081038 A1 | 4/2006 | Platzek et al. | |

FOREIGN PATENT DOCUMENTS

| | | |
|---|---|---|
| RU | 2 229 112 | 5/2004 |
| SU | 794 439 | 1/1981 |
| WO | 2008/148536 | 12/2008 |

OTHER PUBLICATIONS

Authors: Gustavo Luengo, Masaru Tsuchiya, Manfred Heuberger and Jacob Israelachvili, Title: "Thin Film Rheology and Tribology of Chocolate", Date: 1997, Publisher: Journal of Food Science, vol. 62, No. 4, pp. 767-812.*

Authors: S. Lee, M. Heuberger, P. Rousset, and N.D. Spencer, Title: "Chocolate at a Sliding Interface", Date: 2002, Publisher: Journal of Food Science, Institute of Food Technologists, Volume: vol. 67, Nr. 7, pp. 2712-2717.*

(Continued)

*Primary Examiner* — Lisa Caputo
*Assistant Examiner* — Roger Hernandez-Prewitt

(57) ABSTRACT

The invention relates to a method for differentiating foods with respect to mouthfeel, a method for identifying a composition having the ability to improve the mouthfeel of a food, and a method for predicting mouthfeel attributes of a food using a novel tribology device.

14 Claims, 24 Drawing Sheets

OTHER PUBLICATIONS

Ranc et al., "Effect of surface structure on frictional behavior of a tongue/palate tribological system", Tribology International, Butterworth Scientific Ldt., Guildford, GB, Dec. 2006, vol. 39, No. 12, pp. 1518-1526 (XP005609460).

De Wijk et al., "Texture of semi-solids; sensory and instrumental measurements on vanilla custard desserts", J. Food Quality and Preference, 2003, vol. 14, pp. 305-317.

Cutler et al., "Oral perception of viscosity in fluid foods and model systems", Journal of Texture Studies., 1983, vol. 14, pp. 377-395.

Terpstra et al., "Modeling of thickness for semisolid foods", Journal of Texture Studies, 2005, vol. 36, pp. 213-233.

Kokini, J., "The physical basis of liquid food texture and texture—taste interactions", Journal of Food Engineering, 1987, vol. 6, pp. 51-81.

Bourne, M., "Correlation between physical measurements and sensory assessments of texture and viscosity", Food Texture and Viscosity, 2nd Ed., AP,Food Science and Technology, International Series, San Diego, 2002, pp. 315-318.

Lucas, et al., "Food Texture and its Effect of Ingestion, Mastication and Swallowing", Journal of Texture Studies, 2004, vol. 35, pp. 159-170.

Richardson et al.,"Effect of homogenization and fat content on oral perception of low and high viscosity model creams", Journal of Sensory Studies., 1993, vol. 8, pp. 133-143.

De Wijk et al., The role of Friction in perceived oral texture, Food Qual. Prefer., 2005, vol. 16, pp. 121-129.

Malone et al., "Oral behaviour of food hydrocolloids and emulsions. Part 1. Lubrication and deposition considerations", Food Hydrocolloids, 2003, vol. 17, pp. 763-773.

Dresselhuis et al., "Application of oral tissue in tribological measurements in an emulsion perception context", Food Hydrocolloids, 2008, vol. 22, pp. 323-335.

Lee et al., "A tribological model for chocolate in the mouth: General implications for slurry-lubricated hard/soft sliding counterfaces", Tribology Letters, Apr. 2004, vol. 16, pp. 239-249.

Stone et al., Sensory Evaluation Practices—2nd Edition, Chapter 6, 1985, Academic Press: Orlando, FL, pp. 202-242.

Lee et al., "Chocolate at a sliding Interface", Journal of Food Science, 2002, vol. 67, No. 7, pp. 2712-2717.

Kappes, S.M., et al., "Mouthfeel Detection Threshold and Instrumental Viscosity of Sucrose and High Fructose Corn Syrup Solutions", Journal of Food Science, 2006, vol. 71, No. 9, pp. S597-S602.

Akhtar et al., "Perception of creaminess of model oil-in-water dairy emulsions: Influence of the shear-thinning nature of a viscosity-controlling hydrocolloid", Food Hydrocolloids, vol. 20, 2006, pp. 839-847.

Dickenson et al., (2006). Perception of the creaminess of dairy emulsions of well-defined droplet size and controlled rheology. Proceedings of the 4th International Symposium on Food Rheology and Structure P. Fischer, P. Erni & E.J. Windhab, editors (ETH Zürich, ISBN 3-905609-25-8) pp. 293-297.

Luengo et al., "Thin Film Rheology and Tribology of Chocolate", Journal of Food Science, 1997, vol. 62, No. 4, pp. 767-772, 812.

\* cited by examiner

METHODS FOR ASSESSING MOUTHFEEL ATTRIBUTES OF FOODS USING A TRIBOLOGY DEVICE

The invention relates to a method for differentiating foods with respect to mouthfeel, a method for identifying a composition having the ability to improve the mouthfeel of a food, and a method for predicting mouthfeel attributes of a food using a novel tribology device.

Mouthfeel is a food product's physical and chemical interactions in the mouth used to describe the overall texture of a food product. It is a key driver of consumer acceptance and therefore of paramount importance for the food industry. The mouthfeel sensations, however, are complex and cannot be explained by simple physical phenomena.

"Thickness", for example, can only be explained to some degree by viscosity (Cutler et al., *J. Texture Stud.* 14: 377-395 (1983); de Wijk et al., *J. Food Qual. Pref.* 14: 305-317 (2003)) and shear-stress (Terpstra et al., *J. Texture Stud.* 36: 213-233 (2005)) measured using bulk rheological techniques. This finding may be attributed to the fact that several aspects of the complex processes contributing to the human mouthfeel perception during the consumption of foods, such as interactions of the food with saliva and squeezing or compression movements of the tongue towards the palate, are not adequately assessed by rheological measurements.

Another key mouthfeel attribute of food products is the sensory sensation "creamy mouthfeel" or "creaminess" which has been reported to be related to multiple food properties, including smoothness, thickness, and specific flavours (Kokini, J., *J. Food Eng.* 6: 51-81 (1987); de Wijk et al., supra). Creaminess appears to be related to a combination of several factors, including (i) moderate to high viscosity, (ii) non-Newtonian flow, (iii) presence of some fat, and (iv) other factors (Bourne, M., Correlation between physical measurements and sensory assessments of texture and viscosity, in: *Food Texture and Viscosity*, $2^{nd}$ ed., AP, San Diego, p. 317 (2002)). Other factors which have been implicated to influence the creaminess of a food product include, inter alia, the presence of saliva, the viscosities at the food-mucosa interface, and the distribution of fat droplets (Lucas et al., *J. Texture Stud.* 35: 159-170 (2004); Richardson et al., *J. Sensory Stud.* 8: 133-143 (1993)).

Recently, it was found that the lubrication ability or "lubricity" of a food product, as measured using different instrumental techniques, relates to mouthfeel sensations, such as slipperiness (de Wijk et al., *Food Qual. Prefer.* 16: 121-129 (2005); Malone et al., *Food Hydrocolloids* 17: 763-773 (2003); Lucas et al., supra). The lubrication behaviour of food products can, for example, be measured by tribological techniques (Malone et al. (2003), supra), which enables the determination of parameters of interacting surfaces in relative motion, such as the frictional resistance to motion arising from the shearing of a fluid between two surfaces. The lubrication behaviour of foods is generally measured using standard tribology equipment, e.g. a pin-on-disk or a ball-on-disk set up (Malone et al. (2003), supra); Dresselhuis et al., *Food Hydrocolloids* 22: 323-335 (2008)).

Tribological measurements have the advantage to entail the rubbing and squeezing actions of food items occurring between the tongue and palate, which are not measured by rheology. These rubbing and squeezing motions generate a frictional force in which the food-saliva mixture acts as a lubricant. The oral friction can be described with the help of Stribeck curves, i.e. friction factors measured as a function of sliding speed, in which the boundary or mixed regime describe the friction of a food material which is at least in partial contact with each other (Dresselhuis et al., supra).

A highly critical factor in lubrication testing is the properties of the measuring surfaces. Previous studies have employed poly(tetrafluorethylene) (PTFE) and zirconia (Lee et al., *Tribology Letters* 16: 239-249 (2004)) or steel against silicon rubber (Malone et al., supra). However, these surfaces are very smooth and did not closely mimic the properties of the oral tissue of the mouth (Dresselhuis et al., supra). Therefore, in other studies the friction coefficients of foods were determined using a relatively hard ball (steel or PCTFE) representing the palate and a silicone surface with well-defined surface structures simulating the tongue (Ranc et al., *Tribol. Internat.* 39: 1518-1526 (2006)).

Despite extensive research directed to assessing mouthfeel attributes of foods, the current instrumental measuring methods only provide a partial picture of the food systems mouthfeel. For this reason, the characteristics of food products are currently still assessed by scoring defined attributes of a given food by expert panels. These types of sensory studies, however, are very time-consuming and susceptible to a large range of variations.

Thus, it is an object of the present invention to provide a method for physically assessing mouthfeel attributes of foods in a simple, cost-efficient, repeatable and reproducible manner.

In accordance with the present invention, this object is achieved by the methods as described herein below using a novel tribology device. This tribology device allows to generate tribological data in a highly sensitive manner which can be statistically correlated to sensory attributes of mouthfeel. This allows a food product developer to significantly reduce the amount of costly sensory testing since only those food products that have a potential to exhibit a particular mouthfeel attribute need to be passed to a sensory test. Further, the instrumental assessment of mouthfeel attributes using the novel tribology device of the present invention shows excellent repeatability, high reproducibility and ease of operation.

In particular, the methods of the present invention using a novel tribology device opens up the possibility for food product developer's to perform high-throughput screenings of newly developed food products and, thus, to greatly facilitate the development of food products. Specifically, it enables a food formulator to identify compositions, e.g. food ingredients and food ingredient systems, which are able to provide a food with a particular and desired mouthfeel sensation. This is, inter alia, of particular relevance for foods lacking satisfying mouthfeel sensations due to the removal or alteration of ingredients, as for caloric reduction, such as diet beverages, light beverages or low fat food.

In summary, the present invention provides instrumental methods for assessing mouthfeel attributes of foods by means of tribological measurements using a novel tribology device that are complementary to sensory analysis and significantly enhance, facilitate and accelerate a product developer's ability to tailor ingredient systems not only with regard to the desired health and nutritional profiles, but also to the desired mouthfeel.

According to a first aspect of the present invention, there is provided a method for differentiating foods with respect to mouthfeel, comprising the steps of (i) recording a first tribological profile by measuring the friction factor of a first food as a function of sliding speed using the tribology device of the present invention or the rheometer of the present invention comprising such a tribology device, (ii) recording a second tribological profile by measuring the friction factor of a second food as a function of sliding speed using the tribology device of the present invention or the rheometer of the present invention comprising such a tribology device, and (iii) comparing the first tribological profile with the second tribological profile.

The tribology device, which is used herein for assessing mouthfeel-related tribological properties of a food sample (in the following sometimes referred to as tribology device of the present invention) comprises a motor and a measuring system. The measuring system comprises a first measuring element having at least a first measuring surface, and at least a second measuring element separated from the first measuring element and having at least one second measuring surface, wherein at least one of the measuring elements is connected to the motor. The at least one first measuring surface and the at least one second measuring surface define at least one contact measuring surface in which the food sample is disposed and sheared during measurement. The width of said at least one contact measuring surface is adjustable by displacing the first measuring element and the at least one second measuring element relative to each other, i.e. the contact between measuring surfaces is achieved by displacing the at least one first measuring element and the at least one lower measuring element relative to each other.

The tribology device of the present invention is characterized in that at least one second measuring surface, at least one first measuring surface, or both at least one second measuring surface and at least one first measuring surface is (are) composed of a particular thermoplastic elastomer defined herein below, which was unexpectedly found to give highly sensitive friction factor responses. As a result, the tribology device of the present invention is able to readily discriminate even between samples which are not well distinguished by bulk rheology. In other words, the tribology device of the present invention was unexpectedly found to much better discriminate between different food samples compared to bulk rheological measurements. As explained in detail below, the friction and lubrication properties of a food product measured tribologically can be correlated to sensory attributes of the food product. Thus, the tribological profiles recorded by using the tribology device of the present invention allow the differentiation of food products with respect to their sensory mouthfeel attributes.

A preferred embodiment of the tribology device suited for use herein is a tribology device which comprises a motor-driven shaft and a measuring system. The measuring system consists of an upper measuring element connected to the motor-driven shaft and a lower measuring element located at a separation below the upper measuring element, wherein the lower measuring element is preferably fixed. The upper measuring element has a first measuring surface and the lower measuring element has at least one second measuring surface, wherein the first and second measuring surfaces define a contact measuring surface. The width of said contact measuring surface is adjustable by displacing the upper measuring element and the lower measuring element relative to each other, i.e. the contact between measuring surfaces is achieved by displacing the upper measuring element and the lower measuring element relative to each other. During measurement, a sample to be tested is disposed in the contact measuring surface and is sheared between the first and second measuring surfaces, generating a measurable frictional force.

The tribology device according to this preferred embodiment is also characterized in that at least one measuring surface is composed of a particular thermoplastic elastomer as defined herein below. More specifically, at least one second measuring surface of the lower measuring element, the first measuring surface of the upper measuring element, or both the at least one second measuring surface of the lower measuring element and the first measuring surface of the upper measuring element is (are) composed of the thermoplastic elastomer defined herein below.

According to the present invention, thermoplastic elastomers suited for use herein are thermoplastic elastomers having a delta friction factor of more than 0.2 between an aqueous 10% (w/w) sucrose solution and sunflower oil. Preferably, the delta friction is higher than 0.4, and more preferably higher than 0.6. The delta friction factor is defined as the maximum difference between the friction factor of a 10% (w/w) sucrose solution and the friction factor of sunflower oil that occurs at any given sliding speed below 20 mm/s, preferably in the range of 0.4 to 20 mm/s. This is, for example, illustrated in FIG. 4, where $\Delta\mu$ is defined as the friction factor of a 10% (w/w) sucrose solution minus the friction factor of sunflower oil, and $\Delta\mu_{max}$ is defined as the maximum value of $\Delta\mu$ that occurs at any given sliding speed in the range of 0.4 and 20 mm/s.

Preferably, the thermoplastic elastomer used in the tribology device of the invention exhibits a Shore A hardness of 25 to 75, preferably of 30 to 65, more preferably of 35 to 60. The tear strength of the thermoplastic polymer is preferably from 2 to 12 N/mm$^2$, more preferably from 4 to 12 N/mm$^2$, still more preferably from 3 to 10 N/mm$^2$, and most preferably from 6 to 10 N/mm$^2$. Another preferred property of the thermoplastic elastomer is an elongation at break of 500 to 900%, preferably from 550 to 850% and more preferably from 575 to 820%. Moreover, the thermoplastic elastomer preferably exhibits a tear propagation at break of 2 to 35 N/mm, more preferably from 8 to 35 N/mm, still more preferably from 8 to 30 N/mm, and most preferably from 15 to 30 N/mm.

In a preferred embodiment, the thermoplastic elastomer used exhibits the following properties: a Shore A of 50, a tear strength of 7.7 N/mm$^2$, an elongation at break of 576% and a tear propagation at break of 24.8 N/mm. In another preferred embodiment, the thermoplastic elastomer exhibits the following properties: a Shore A of 59, a tear strength of 10 N/mm$^2$, an elongation at break of 800% and a tear propagation at break of 16 N/mm.

In addition, the thermoplastic elastomer used herein should remain fixed to the measuring element at sliding speeds of up to 250 mm/s and be mechanically stable, i.e. it should not erode or wear by the rotating measuring element. Suitably, it is also chemically stable, i.e. inert towards the sample to be tested, in particular food ingredients, such as oils and acids. Further, while the measuring surface of the thermoplastic elastomers is preferably smooth, also thermoplastic elastomers having rough surfaces may be employed, if desired or needed, which result in an increased friction signal. The surface may be designed into precisely controlled topographical features. It may, for example, exhibit a plurality of well-defined "hills" of "pillars" with a height of 20-250 μm, preferably 50-100 μm. Furthermore, a thermoplastic elastomer suited for use within the present invention preferably shows no slipperiness or twisting, which may give rise to signal discontinuities (i.e. a sharp increase or decrease in the Stribeck curve), or cross over effect (i.e. a higher friction for sunflower oil than for 10% (w/w) sucrose at high sliding speeds) during tribology testing. An averaged skilled person will be able to select an appropriate thermoplastic elastomer for use herein taking into account the above mentioned factors and considering the appended Examples.

Particular suitable thermoplastic elastomers for use herein are thermoplastic elastomers based on hydrogenated or styrene block copolymers (HSBC), in particular those made up of thermoplastic polystyrene end blocks and elastic midblocks of, for example, ethylene-butylene or ethylene-propylene. Specific examples of such hydrogenated styrene block copolymers include hydrogenated styrene/butadiene/styrene block copolymers (SBS), styrene/ethylene-butylene/styrene (SEBS), styrene/ethylene/styrene block copolymer (SES), styrene/ethylene-propylene/styrene block copolymer (SEPS), hydrogenated styrene/isoprene block/styrene block copolymer (SIS), and the like.

In the following the tribology device used herein is further described by referring to the described preferred embodiment of the tribology device. However, that description also applies to the described embodiment of the tribology device which has at least a first measuring surface and at least a second measuring surface. In particular, any reference to the "upper measuring element" of the preferred embodiment of the tribology device is to be understood to also refer to the "first measuring element" of the other embodiment of the tribology device described above, and any reference to a "lower measuring element" of the preferred embodiment of the tribology device is to be understood to also refer to the "second measuring element" of the other embodiment of the tribology device described above.

For adjusting the normal force, which controls the width of the contact measuring surface, at least one of the upper measuring element or the lower measuring element is displaced in coaxial direction relative to the motor-driven shaft by a lifting device. Preferably, the upper measuring element can be moved up and down by means of said lifting device. After having disposed a sample in the contact measuring surface, the upper and lower measuring elements are displaced relative to each other to result in a normal load of 1 to 10 N, preferably 2 to 4 N.

Further, the tribology device of the invention preferably comprises at least one heating element for heating at least one of the first or second measuring surfaces since a homogeneous temperature of the sample inside the contact measuring surface may be important for measuring tribological properties, such as friction coefficients. Preferably, the heating element is a Peltier element arranged below the lower measuring element and/or at the upper part. Moreover, the heating elements may be at least partially surrounded by a hood, such as a Peltier hood, for reasons of thermal insulation.

The shaft to which the upper measuring element is connected is rotated by a motor and typically mounted in a guide bearing. Preferably the tribology device contains an element for measuring the rotation frequency and/or the phase position, which allows together with the supply parameter, in particular the current consumption, to calculate the friction force. The measurement values can be evaluated in a control or evaluation unit, which senses the supply parameters of the motor, sets the width of the contact measuring surface, and comprises suitable recording and display appliances.

In accordance with the invention, the sample to be tested is a food, food sample or food product, respectively. The term "food" used herein, either alone or in combination with another noun, includes any foodstuff, including beverages, intended to be ingested by animals or humans. Examples of foods which are of particular relevance in connection with the present invention include chocolate, in particular light chocolate, beverages, such as carbonated beverages and cola beverages, low caloric beverages, light caloric beverages, such as light beer, nutritional beverages, such as dairy drinks, thick products, such as dressings, sauces, spreads, frozen dessert mixes, baby food and soups and sauces, and ingredients for food formulations such as oils, water soluble fibers, sweeteners, proteins, hydrocolloids, and the like.

In a preferred embodiment, the upper measuring element is ball-shaped or an at least partially spherical body like a hemispherical body, and connected to the motor-driven shaft by, for example, means of a fixture. The selection of suitable materials for the upper measuring element depends on the same factors as for the lower measuring element, i.e. chemical and physical stability, high friction sensitivity (i.e. a maximum friction factor difference as defined above), and the absence of slipping, twisting or cross over effects, as described herein above. It may also have a smooth or rough first measuring surface.

Preferably, the upper measuring element is made of stainless steel. However, in case of samples that are capable of corroding stainless steel it may be made of another inert material, such as a thermoplastic elastomer and the like. In case a thermoplastic elastomer is used as material of the upper measuring element, the one as defined herein above may be applied, including those having smooth or rough measuring surfaces. In other words, the at least one second measuring surface is preferably made of a thermoplastic elastomer as defined herein and the upper measuring element or the first measuring surface, respectively, is preferably made of stainless steel (or any other suited material) or vice versa. Further, also both the first measuring surface and the at least one second measuring surface are made of the thermoplastic elastomer defined herein above.

In another preferred embodiment, the lower measuring element includes a support member and, supported thereon, one or more substrates composed of the thermoplastic elastomer described herein. Each of the one or more substrates has a second measuring surface facing the first measuring surface of the upper measuring element. During measurement the sample is sheared between the first surface of the upper measuring element and the second measuring surfaces provided on each the one or more substrates. Typically, the one or more substrates protrude from the support member in a direction towards the upper measuring element. Thus, depending on the number of substrates, the lower measurement element provides a n-point and/or n-area contact measuring geometry, wherein n is the number of substrates.

The one or more substrates are permanently or releasably attached to the support member by means known to a skilled person, for example by introducing the substrates into grooves formed in the surface of the support member facing the upper measuring element, by means of adhesives, or by coating the support member with the substrate. Conveniently, the one or more substrates are releasably fastened to the support member, for example, by placing the one or more substrates into grooves formed in the surface of the support member facing the upper measuring element.

Preferably, the one or more substrates are present in the form of plates or strips, the surface(s) of which define a contact measuring surface with the first measuring surface of the upper measuring element. Preferably, the elastomer strips are cut into shapes of 0.6 mm width and 1.6 mm length and have a thickness of from about 1.79 mm to 2.11 mm. More preferably, at least two plates or strips are employed. The plates or strips can be located in a plane perpendicular to the motor-driven shaft. More preferably, the two or more plates or strips extend from the projection of the motor-driven shaft and are inclined relative to the projection of the motor-driven shaft with their more distant ends, relative to the projection of the motor-driven shaft, pointing towards the upper measuring element, wherein the angle between the plates or strips and the coaxial projection direction of the motor-driven shaft is between 1 and 80°, preferably 10 to 70°, more preferably 30 to 55°. Further, when viewed along the direction of the motor-driven axis towards the lower measuring element, the at least two plates or strips are preferably evenly spaced and arranged around the projection of the motor-driven shaft. In a particular preferred embodiment of the present invention three plates or strips are used as the at least two plates or strips, forming a three-point contact geometry of the lower measuring element.

A particular preferred design of the measuring system of the tribology device of the invention has a ball-on-three plates contact geometry. In this particular geometry, the upper measuring element is ball-shaped, and is in particular a ball made of stainless steel. The lower measurement element consists of a support member and three plates of the above-defined thermoplastic elastomeric material attached to the support member, preferably by means of grooves formed in the surface of the support member facing the upper measuring element.

Also suitable for use herein are measuring systems with a similar structure as the above-described ball-on-three plates geometry, but with two or four and more plates each coming in sliding contact with the sample disposed between the first surface of the upper ball-shaped measuring element and the second surfaces provided by the two or four and more plates of the lower measuring element.

The tribology device described above may be used with a commercial rheometer, in particular a small-stress rheometer. Basic designs of rheometers are, for example, described in US 2006/0081038 A1, U.S. Pat. No. 6,571,610 B1 and U.S. Pat. No. 6,499,336 B1.

The method according to the first aspect of the invention is particularly useful in differentiating food products which are related to each other. In other words, the above-mentioned first and second foods of the method according to the first aspect of the invention are preferably related food products. The term "related food products", as used herein, is intended to mean food products of the same sub-group, category or type, which are similar with respect to their composition and sensory attributes. In particular, the term "related food products" refers to similar but sensorially distinguishable varieties of a particular food item, in particular of the foods defined hereinbefore, such as different kinds of mayonnaises, dressings, dairy products, e.g. different drinking yogurts, ice cream, whey beverages, light beverages, fruit juices, ice creams and, different kind of chocolates and the like.

According to a second aspect of the present invention, there is provided a method for identifying a composition, selected from foods, food ingredients, ingredient blends or systems of ingredients, which is able to provide mouthfeel sensations to a given food and/or improve mouthfeel sensations of a given food which lacks in these sensations, comprising the steps of (i) obtaining a first target tribology profile by measuring the friction factor of a first food having desirable mouthfeel sensations as a function of sliding speed using the tribology device of the present invention or the rheometer of the present invention comprising such a tribology device, (ii) obtaining a second tribology profile by measuring the friction factor of a second food using the tribology device of the present invention or the rheometer of the present invention comprising such a tribology device, wherein the second food is a mixture of the given food lacking and/or being inferior in one or more of the desirable mouthfeel sensations of the first food and the composition to be identified, (iii) comparing the first target tribology profile with the second tribology profile, and (iv) identifying the composition being able to provide mouthfeel sensations to the given food lacking in these sensations, which results in a second tribology profile that is substantially equivalent to the first target tribology profile.

According to the present invention, the term "systems of ingredients" may include a combination of ingredients to substitute sucrose in light beverages, a combination of hydrocolloids to meet certain behaviour, or a combination of fat replacers in low caloric products. Other examples of "systems of ingredients" may be emulsified fat droplets, with the systems comprising fat, oils, lipophilic food ingredients or either mixtures; an emulsifier or emulsifiers, an interfacial stabilizer, such as a protein or carbohydrate, such as pectin or chitosan. Another example is a mixture comprising carbohydrates and gums, such as xanthan, and carbohydrates, such as trehalose, that effectively interact with saliva and oral tissues to alter the oral surfaces and lubrication properties. Other examples are mixtures of food plasticizers and solvents, such as glycerine and propylene glycol. Yet other examples are mixtures of food biopolymers such as glycoproteins (casein macropeptide), proteins (egg albumin), gums (carrageenan, guar, locust bean, gellan, etc.), fibers, starches (corn, potatoe, wheat) and their hydrolyzates.

The term "substantially equivalent" tribology profile, as used herein, is intended to mean a tribology profile of a food which is identical or highly similar to another tribology profile of another food and which results in substantially equivalent sensory profiles. According to the present invention, a "substantially equivalent" sensory profile is a sensory profile of a food which is identical or highly similar to another sensory profile of another food, wherein a sensory profile is "highly similar" if no detectable differences (percent discriminators below 50%) in standard consumer difference tests using standard sensory evaluation methods, for the specific mouthfeel attributes are identified as related to lubrication for the products being tested.

According to a third aspect of the present invention, there is provided a method for predicting sensory mouthfeel attributes of a food, comprising the steps of (i) obtaining a tribological data set by measuring the friction factor of a food as a function of sliding speed using the tribology device according to the present invention or the rheometer of the present invention comprising such a tribology device, and (ii) determining one or more sensory mouthfeel attributes of the food based on a predetermined correlation model which correlates tribology data of the food and sensory data of the food to predict the one or more sensory mouthfeel attributes.

The predetermined correlation model is established by the following sub-steps (iii) to (vi): (iii) defining one or more sensory mouthfeel attributes of a reference food by a sensory analysis, (iv) collecting a sensory data set by sensorially scoring the reference food in terms of the one or more sensory mouthfeel attributes defined in step (iii), (v) collecting a tribology data set by measuring the friction factor of the reference food as a function of sliding speed using the tribology device of the present invention or the rheometer of the present invention comprising such a tribology device, (vi) building up a correlation model between the tribological data set obtained in step (v) and the sensory data set obtained in step (iv) to predict the one or more sensory mouthfeel attributes. The reference food and the food whose sensory mouthfeel attributes are to be predicted are usually related food products, wherein the term "related food products" has the meaning as defined hereinbefore.

In a typical measurement of friction factor as a function of sliding speed in accordance with the present invention, the friction factors are recorded at sliding speeds in a range of 0.4 and 250 mm/s. A constant load of 1 to 10 N, preferably 2 to 4 N, typically 3 N, is preferably used. The measurement temperature depends on the nature of the food investigated but is usually in the range of 4° C. to 50° C., preferably 6° C. to 45° C., more preferably 15° C. to 45° C., and yet more preferably 15° C. to 37° C. For some applications, such as creams and mayonnaises, the temperature needs to be lowered to 12° C. However, for most applications the temperature is typically 20° C. Prior to the recording of Stribeck curves, the food samples are preferably pre-sheared at 0.4 mm/s for 10 min to condition the shear history of the food sample.

Any feature of any aspect of any embodiment described herein, including the features disclosed in the claims and the figures may be combined with any such feature to give embodiments of the present invention which may be capable of being protected as such.

The present invention will now be described in more detail by reference to the following detailed description of a preferred embodiment of the tribology device of the invention, the Examples and the accompanying drawings, in which.

Figure 1:
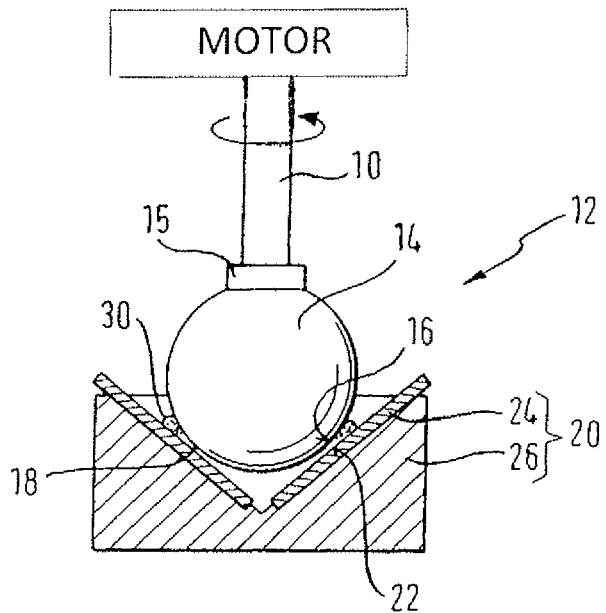
FIG. 1 is a fragmentary sectional side-view of a preferred embodiment of the tribology device in accordance with the present invention and schematically illustrates the ball-on-three-plates principle of the measuring system.
Figure 2:
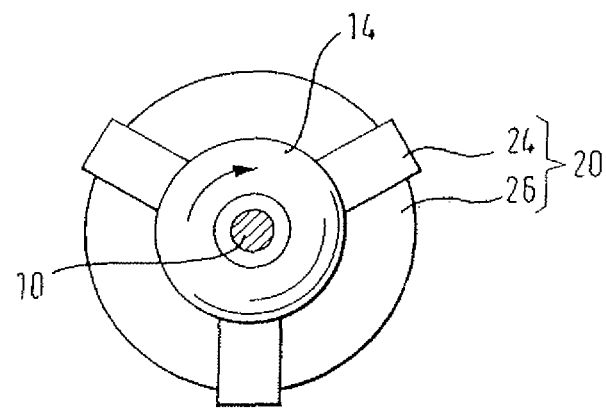
FIG. 2 is a schematic cross-sectional top-view along the motor-driven shaft of the embodiment of the tribology device shown in FIG. 1 onto the ball-on-three-plates measuring geometry.
Figure 3:
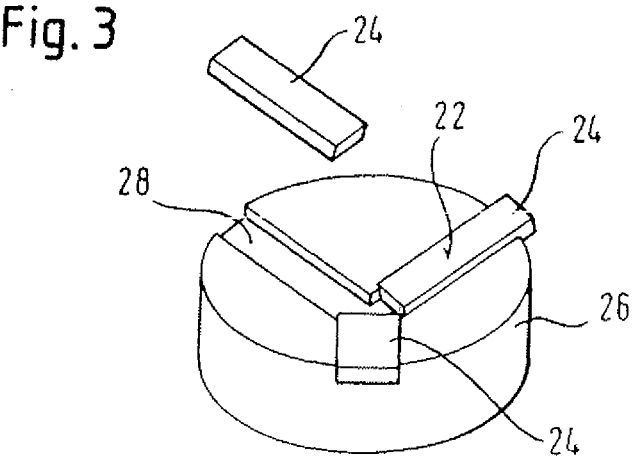
FIG. 3 is a schematic view of the lower measuring element, on an enlarged scale, and illustrates further aspects of the ball-on-three-plates measuring system shown in FIGS. 1 and 2.

In accordance with FIG. 1 and FIG. 2, a preferred embodiment of the tribology device of the invention has a ball-on-three-plates measurement geometry in which a ball is rotated over a three-point contact area formed by three plates of a thermoplastic elastomer substrate. More specifically, the tribology device comprises a motor-driven shaft 10 and a measuring system 12. The measuring system 12 consists of a ball-shaped upper measuring element 14, preferably made of stainless steel, which is connected to the motor-driven shaft 10 by a fixture 15, and a lower measuring element 20, which includes a support member 26, for example made of stainless steel, and three plates or strips 24 of a thermoplastic material as defined hereinbefore. As depicted in FIG. 3, the plates or strips 24 may be placed in grooves 28 formed in the surface of the support member 26 facing the upper measuring element 14, thereby releasable fastening the plates or strips 24 to the support member 26.

For measuring the tribological properties of a food sample 30, the sample 30 is placed onto the lower measuring element 20, and the upper measuring element 14 and the lower measuring element 20 are vertically displaced relative to each other by a lifting device (not shown) until a contact measuring surface 18 of a desired width is set. The upper measuring element 14 is rotated by a motor (not shown) and shears the sample 30 between the first measuring surface 16 of the ball-shaped upper measuring system 20 and the second measuring surfaces 22 provided on the plates or strips 24 (three-point contact area). During measurement at least one of the upper and lower measuring elements 14, 20 are preferably temperature-controlled by a heating element, such as a Peltier element (not shown).

The present invention is further illustrated by the following Examples.

EXAMPLES

Example 1

Selection of Thermoplastic Elastomers and Corks (Upper Measuring Elements)

1. Selection of Thermoplastic Elastomers
1.1 Determination of Chemical Stability The thermoplastic elastomers forming the second measuring surface of the lower measuring element of the tribology device of the present invention should be inert towards the sample to be examined during the experimental time-frame.

Therefore, the chemical stability of the thermoplastic elastomers in oil was evaluated by soaking strips from different materials in sunflower oil for 6 days. The variation of the strips weight was recorded on an analytical balance (Mettler Toledo AG 135, 0.1 mg) before and after soaking (and after exhaustive blotting with an oil-absorbing tissue for the latter). If the material looses weight in this stability test, this is probably due to the diffusion of oil-soluble compounds from the thermoplastic elastomer (e.g. plasticising oil and/or lubricating silicone) to the sunflower oil. Although such a material is not recommended for long-term exposure, it does not preclude its use as disposable material in single-use tribological experiments.

In addition, the chemical stability of the thermoplastic elastomers in acidic, aqueous solution was evaluated by soaking strips from different materials in 0.1 M citric acid/Na citrate buffer (pH 3.0) for 14 days. The variation of the strips weight was recorded on an analytical balance (Mettler Toledo AG 135, 0.1 mg) before and after soaking (and after exhaustive blotting with an absorbing tissue for the latter). If the material gains weight, this is probably due to extensive swelling. Again, although it is not recommended for long-term exposure, it does not preclude its use as disposable material in single-use experiments.

1.2 Determination of Friction Factor

The determination of friction factor was carried out to identify the most discriminating and sensitive elastomer type. All tribology measurements were carried out on a MCR-301 rheometer (Anton Paar, Stuttgart, Germany) using a tribology device of the present invention with a measuring system of the ball-on-three-plates geometry (see FIGS. 1-3), which was temperature controlled by a peltier and hood temperature control system. This tribology device employs stainless steel ball which is rotated over a contact area comprising 3 grooves, where 3 interchangeable strips of elastomer substrates are placed.

The test temperature was set at 20° C. with an initial non-recording pre-shear of 0.4 mm/s for 10 min followed by recording the friction coefficient as a function of sliding speed (0.4 to 250 mm/s) at constant load of 3 N. The friction force $F_R$ is measured as a function of sliding speed. The friction factor or coefficient ($\mu$) was calculated as the ratio of friction force to normal force $F_R/F_N$ for each elastomer type.

The friction factor ($\mu$) was measured on sunflower oil and 10% (w/w) sucrose solution. $\Delta\mu$ is defined as the friction factor of a 10% (w/w) sucrose solution minus the friction factor of sunflower oil. $\Delta\mu_{max}$ is defined as the maximum value of $\Delta\mu$ that occurs at any given sliding speed in the range of 0.4 and 20 mm/s.

Figure 4:
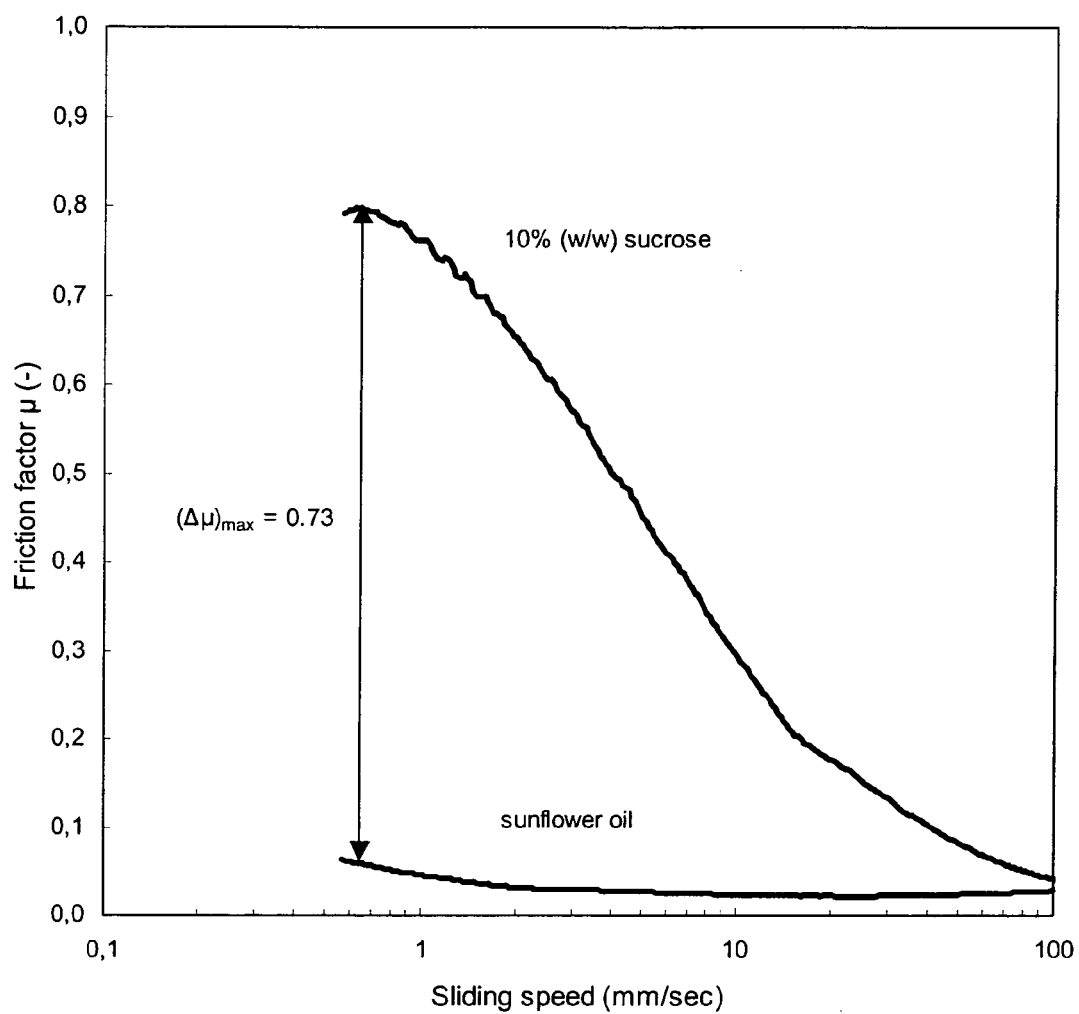
FIG. 4 is a chart showing the determination of delta friction factor $(\Delta\mu)_{max}$.

FIG. 4 shows exemplary Stribeck curves of friction factor versus sliding speed for sunflower oil and 10% (w/w) sucrose solution and the maximum friction factor difference ($\Delta\mu_{max}$).

1.3 Determination of Mechanical Stability
1.3.1 High Friction Strips Surfaces

For a food system studied using a given strips plus upper ball-shaped element combination, the friction factor signal should be free of any sharp discontinuities, i.e. a sharp increase or decrease in the Stribeck curve. While not being bound by theory, it is believed that these signal discontinuities are not originating from instrumental noises (i.e. signal-processing related) but arise from either the slipping of the upper ball-shaped element over one of the interchangeable strips, or a local deformation (e.g. twisting) of one of the interchangeable strips. This is to say, that this phenomenon is likely to be due to the combination of a high friction of the strips surface associated with the poor lubricating properties of the food system under investigation. However, it should be appreciated that strips with a high friction factor surface that are not suitable for a poor lubricating food system are potentially suitable when assessing the tribological profile of a good lubricating food system.

1.3.2 Rotation-Induced Erosion of Strips

For any tribological experiment, the strips should not show any sign of erosion or embossing after use. Thus, the strips should be visually observed as is or with a low magnifier.

1.4 Hardness (Shore A) and Tensile Strength as Thermoplastic Elastomer Selection Criteria The $\Delta\mu_{max}$ of 32 elastomer strips made from Kraiburg TPE (TPE=thermoplastic elastomer) (KRAIBURG TPE GmbH, Waldkraiburg, Germany) (2 mm thickness, smooth surface) was determined (see Table 1).

The Pearson's correlation coefficient and its level of significance was calculated for the entire population of 32 TPEs. For this population, decreasing elastomer hardness is correlated with increasing $\Delta\mu_{max}$ at 0.5% significance level. At 1% significance level, decreasing tensile strength is correlated with increasing $\Delta\mu_{max}$.

In conclusion, both the material hardness (Shore A) and its tensile strength could be used for strips selection. Preferably, the material hardness (Shore A) is used for strips selection.

TABLE 1

Properties of thermoplastic elastomers used for strips selection

| No. | TPE | Hardn. (Shore A) | Tensile strength (N/mm$^2$) | Elon. at break (%) | Tear resistance (N/mm) | $\Delta\mu_{max}$[1] | Sliding Speed[2] | Cluster 1 | Cluster 2 | Cluster 3[3] | Cluster 4[4] |
|---|---|---|---|---|---|---|---|---|---|---|---|
| 1 | TA5AOZ | 50 | 2.8 | 480 | 12 | 0.27 | 0.5 | | | x | |
| 2 | TA4AON | 40 | 2 | 500 | 8.5 | 0.18 | 0.5 | | | x | |
| 3 | TC3CSN | 30 | 3.4 | 420 | 12 | 0.18 | 0.5 | | | x | |
| 4 | TC5CSN | 50 | 5.8 | 460 | 16 | 0.27 | 4.1 | x | | | |

TABLE 1-continued

Properties of thermoplastic elastomers used for strips selection

| No. | TPE | Hardn. (Shore A) | Tensile strength (N/mm²) | Elon. at break (%) | Tear resistance (N/mm) | $\Delta\mu_{max}$[1] | Sliding Speed[2] | Cluster 1 | Cluster 2 | Cluster 3[3] | Cluster 4[4] |
|---|---|---|---|---|---|---|---|---|---|---|---|
| 5 | TC3GPN | 30 | 4.8 | 680 | 8 | 0.47 | 1.3 | x | | | |
| 6 | TC5GPN | 50 | 6.2 | 650 | 14 | 0.18 | 5.4 | | | x | |
| 7 | TF4AAB | 42 | 7 | 700 | 29 | 0.38 | 0.5 | x | | | |
| 8 | TF9AAB | 96 | 17 | 650 | | 0.17 | 13.3 | x | | | |
| 9 | TF6AAF | 59 | 10 | 800 | 16 | 0.67 | 4.8 | | x | | |
| 10 | TF2ATL | 25 | 2.5 | 720 | 4 | | | | | | A |
| 11 | TF6ATL | 60 | 10 | 840 | 16.5 | 0.68 | 16.8 | | x | | |
| 12 | TF2BNB | 25 | 2.5 | 625 | 11 | 0.90 | 2.0 | | | | B |
| 13 | TF3BNB | 35 | 6.5 | 835 | 13 | 0.76 | 0.7 | | | x | |
| 14 | TF4BNB | 45 | 7 | 800 | 15 | 0.33 | 0.5 | | | x | |
| 15 | TF5BNB | 55 | 7.5 | 790 | 17 | 0.25 | 0.9 | x | | | |
| 16 | TF6BNB | 65 | 8 | 725 | 20 | 0.19 | 0.8 | x | | | |
| 17 | TF5EFA | 50 | 13.7 | 620 | 28.1 | 0.30 | 0.6 | | | x | |
| 18 | TF5EFC | 50 | 10.2 | 545 | 24.3 | 0.35 | 0.5 | x | | | |
| 19 | TF5EFD | 50 | 7.7 | 576 | 24.8 | 0.43 | 8.9 | x | | | |
| 20 | TF1SNT | 10 | 1 | 400 | 2.5 | | | | | | C |
| 21 | TF3STE | 35 | 6.5 | 740 | 10.5 | 0.40 | 3.0 | | | x | |
| 22 | TF4STE | 45 | 9 | 820 | 17 | 0.31 | 3.5 | x | | | |
| 23 | TF5STE | 55 | 10 | 750 | 24 | 0.40 | 6.3 | x | | | |
| 24 | TF2STL | 14 | 1.2 | 500 | | 1.03 | 3.5 | | | | B |
| 25 | TF2STT | 20 | 0.7 | 500 | | 1.49 | 7.8 | | | | B |
| 26 | TF4THT | 40 | 3.5 | 610 | 14 | 1.37 | 3.3 | | | | B |
| 27 | TF4TTT | 40 | 4 | 560 | 9 | 1.37 | 4.0 | | | | B |
| 28 | TV5LVZ | 50 | 4.7 | 520 | 12.4 | 0.30 | 2.1 | | | x | |
| 29 | TV6LVZ | 60 | 6 | 470 | 15 | 0.17 | 2.1 | | | x | |
| 30 | TF7WKA | 72 | 10 | 750 | 32 | 0.36 | 0.7 | x | | | |
| 31 | STX 1021/46 | | | | | 0.28 | 4.5 | x | | | |
| 32 | HTF 8654/94 | 40 | 3.8 | 811 | | 0.50 | 13.3 | | x | | |

[1] = Maximum friction factor difference between 10% (w/w) sucrose solution and sunflower oil
[2] = Sliding speed where $\Delta\mu_{max}$ occurs
[3] = Cross-over (i.e. higher sunflower oil friction than 10% (w/w) sucrose solution friction at high sliding speeds)
[4] = unusable (technical problems)
A = too soft, does not remain in place
B = slippery signal
C = too sticky, does not remain in place 1.5 Selection of Suitable Thermoplastic Elastomers by Clustering The 32 elastomer strips made from Kraiburg TPEs were clustered into 4 classes, among them clusters 3 and 4 are unsuitable:
Cluster 1 (12 out of 32): characterized in that $\Delta\mu_{max}$ occurs in the plateau region located at the lowest sliding speed;
Cluster 2 (3 out of 32): characterized in that $\Delta\mu_{max}$ occurs as an apex that is located at medium sliding speed around 10 mm/s;
Cluster 3 (10 out of 32): characterised by a "cross-over" at high sliding speed, where the friction of sunflower oil becomes higher than the friction of the 10% (w/w) sucrose solution; and
Cluster 4 (7 out of 32): characterised by (i) high friction surfaces ($\Delta\mu_{max}$ range 0.90-1.49, average 1.23, n=5) giving signal discontinuities with 10% (w/w) sucrose solution or (ii) very soft elastomers that do not hold in place.

From the suited elastomers of clusters 1 and 2, the thermoplastic elastomers with a high sensitivity, i.e. a $\Delta\mu_{max}$ of 0.43 to 0.68, are soft elastomers with a Shore A of between 30 and 60 selected from TF5EFD and TC3GPN (from cluster 1) and HTF 8654/94, TF6AAF and TF6ATL (from cluster 2). These five thermoplastic elastomers are particularly suited for use herein, in particular for foods with a water continuous phase (TC3GPN, TF6AAF and TF6ATL are also suited for foods with an oil continuous phase, whereas HTF 8654/94 and TF5EFD are less suited because of a high weight loss in the above-described stability test in sunflower oil) (see Table 1, where these five thermoplastic elastomers are highlighted in bold).

It is to be pointed that it is important to check experimentally the relaxation time of the elastomer strips after a tribological experiment. With this information, the frequency of strips usage within a working day can be estimated. This is essential to avoid friction factor shifts due to elastomer strips shear history. Further, if needed, there is the possibility to use strips with rough surfaces, leading to an increased friction signal.

2. Selection of Corks (Upper Measuring Elements)

2.1 Determination of Chemical Stability

The chemical stability of steel balls was assessed by soaking same in 0.1 M citric acid/Na citrate buffer (pH 3.0, pH 4.0, pH 5.0 and pH 6.0) and standardised tap water (as reference) for 14 days. No weight variations were recorded, no change in colour was observed. Hence, the steel balls are suitable for repeated use in acidic media (up to pH 3.0).

Further, the stability of steel balls in a carbonated soft drink (Gatorade®) was examined. It was found that the upper ball-shaped element made of steel was converted into a Janus head with one face intact (the face that is not in contact with the beverage) and the other face, in direct contact with the beverage, being strongly eroded (iron-etching, presumably by a chelating compound in the soft drink). Thus, in certain tribological tests, an upper ball-shaped element moulded from an inert material (e.g. plastic, thermoplastic elastomer, etc.) should be used in place of the steel ball.

2.2 Strips/Corks Combinations Screening

With a background of potential erosion of the steel corks (see point 2.1), 7 corks made of plastic or thermoplastic elastomer materials were extruded, moulded and run on the tribometer.

Due to the large number of possible strip/cork combinations, the friction factor difference was measured in duplicate at 2 sliding speeds, 1 and 10 mm/s, respectively. In an experimental design comprising 56 combinations (8 different strips×7 different corks), the higher friction factor difference was observed at 10 mm/s. This data was used to select appropriate strip/cork combinations. The most appropriate range for the strip/cork selection is $0.20 < \Delta\mu < 0.90$, that is (a) not too high to avoid mechanical instability (signal discontinuities) and (b) not too low to avoid poor signal sensitivity.

It is noted that also in the case of corks, corks having a rough surface may be used. Such surfaces may be, for example, manufactured by sand blasting.

Example 2

Correlation of Perceived Mouthfeel in Fluid Dairy Products with Lubricity

The aim of the experiments underlying this example was to assess the influence of fat content of typical dairy products by tribological measurements, bulk rheological methods, and human sensory evaluation to better understand and predict key mouthfeel perceptions in dairy emulsions.

In order to achieve this aim, various fluid dairy products, with varying amounts of fat, were studied using dynamic shear rheology and tribology. Tribological and rheological properties were compared to the sensory assessment of key attributes of dairy samples such as "creaminess", "thickness", "slipperiness", and "smoothness".

It was found that fluid dairy products with varying fat contents can be well differentiated using tribological measurements but not with rheological measurements. Tribological measurements were shown to correlate well with the key mouthfeel attributes of "slipperiness" and "creaminess".

Thus, the origins of mouthfeel sensations in fluid dairy emulsions are found to be strongly related to lubricity.

1. Experimental Procedures 1.1 Material

Commercially available dairy products were purchased at a local supermarket. These fluid dairy products varied in fat content (0 to 12% fat). The composition of each dairy emulsion is shown in Table 2.

TABLE 2

Composition of model dairy emulsions

| Product | Description | Ingredients | Total fat (g) |
|---|---|---|---|
| Heavy whipping cream | Heavy whipping cream, ultra-pasteurized | Heavy cream, skim milk, contains less than 1% of the following: mono and diglycerides, polysorbate 80 and carrageenan | 5 g in 15 ml 33.33% |
| Half & half | Traditional half & half, ultra-pasteurized | Milk, cream, contains less than 1% of the following: sodium citrate and disodium phosphate | 3 g in 30 ml 10% |
| Whole milk | Grade A, pasteurized, homogenized | Milk, vitamin D3 | 8 g in 240 ml 3.33% |
| 2% reduced fat milk | Grade A, pasteurized, homogenized | Reduced fat milk, vitamin A palmitate and vitamin D3 | 5 g in 240 ml 2.08% |
| Fat free skim milk | Grade A, pasteurized, homogenized | Fat free milk, vitamin A palmitate and vitamin D3 | 0 g in 240 ml 0% |

1.2 Rheological Measurements

The influence of composition on the dynamic flow properties of the fluid dairy emulsions with varying fat content was measured using a constant stress rheometer (Anton Paar MCR-301, Stuttgart, Germany) using the cylindrical double-gap configuration (DG-26.7). The dairy samples were placed in the measurement cell of the rheometer and allowed to equilibrate at 20° C. for 10 min. Flow curves were generated by increasing the shear rate of the instrument from $0.5\ s^{-1}$ to $200\ s^{-1}$ and plotting the viscosity as a function of shear rate.

1.3 Tribological Measurements

All tribology measurements were carried out on a MCR-301 rheometer (Anton Paar, Stuttgart, Germany) using a tribology device of the present invention with a measuring system of the ball-on-three-plates geometry (FIGS. 1-3), which was temperature controlled by a peltier and hood temperature control system. This tribology device employs stainless steel ball which is rotated over a contact area comprising 3 grooves, where 3 interchangeable strips of substrates are placed. The substrates are made of a thermoplastic elastomer (TF6AAF material, available from KRAIBURG TPE GmbH, Waldkraiburg, Germany) which has the ability to well discriminate between the dairy samples to be tested.

The test temperature was set at 20° C. with an initial non-recording pre-shear of 0.4 mm/s for 10 min followed by recording the friction coefficient as a function of sliding speed (0.4 to 250 mm/s) at constant load of 3 N. The friction force $F_R$ is measured as a function of sliding speed. The friction factor or coefficient $\mu$ was calculated as the ratio of friction force to normal force $F_R/F_N$.

1.4 Sensory Measurements

Descriptive Analysis

The sensory properties of the samples were investigated using a panel trained in the principles of quantitative descriptive analysis (QDA) as described by Stone & Sidel (Stone & Sidel, *Sensory Evaluation Practice*, Academic Press: Orlando, Fla., (1985)). Panelists were selected from a group of healthy candidates from 18 to 60 years of age. Selection tests included screening for acuity in the basic tastes and the panelist's abilities to assess fattiness, roughness and particle size of a set of texturally diverse samples. Twelve panelists with above average scores on all of the tests were selected for the training. The testing was performed in the sensory facilitates of the Cargill Global Food Technology Center in Minnesota, USA.

The panel was trained during five 2-hour sessions, with a variety of commercial fluid dairy products to generate a set of descriptors for mouthfeel and after effect. Attributes were arranged on the ballot according to the chronological order in which they are perceived (see Table 3). Focus groups were held to discuss the rating of each attribute and further clarify the meaning of the attributes before the actual samples were evaluated.

TABLE 3

QDA mouthfeel descriptors of sample fluid dairy products

| ATTRIBUTE | DESCRIPTION |
| --- | --- |
| MOUTHFEEL Initial: | |
| Temperature | Degree to which sample feels cold in the mouth; warm - cold. |
| Thickness | Degree to which sample feels thick as opposed to thin and watery; thin - thick. |
| Silky | Degree to which surface of sample feels slippery or silky; low - high. |
| Oily | Amount of oily, fatty, or greasy feeling in sample; low - high. |
| Middle: | |
| Heavy | Degree to which sample feels heavy or dense (weight); light - heavy. |
| Homogeneous | Degree to which sample is well blended, being consistent, uniform, or homogeneous throughout; less - more. |
| Creamy | Degree to which sample feels creamy; low - high. |
| Grainy | Degree to which sample feels grainy; smooth - grainy. |
| Tingling | Degree to which tingling sensation is felt in the mouth from sample; low - high. |
| Coats mouth | Degree to which sample coats mouth and back of throat; low - high. |
| Salivating | Degree to which sample causes salivation in the mouth; low - high. |
| Later: | |
| Rate of disappearance | Total time required for sample sensations to leave mouth; short - long. |
| AFTER EFFECTS (Sample removed from mouth) | |
| Lingering | Degree to which sensation of sample lingers after removed from mouth; low - high. |
| Residue Remaining | Degree to which residue remains after sample removed from mouth; low - high. |
| Dryness | Degree to which mouth feels dry after sample removed; low - high. |

Tasting Procedure

Panelists were seated in sensory booths with appropriate ventilation and lighting. The panel evaluated 5 dairy samples in triplicate in a single session. Each food was taken into the mouth and mouthfeel attributes were rated in the order in which they were perceived. The products were swallowed or expectorated and the after-feel attributes rated. Between each sample, panelists were asked to consume a small portion of unsalted cracker and then to rinse the mouth with water.

Panelists' responses were collected using computerized ballots and SIMS 2000 v6.0 software (Sensory Computer Systems, Morristown, N.J., USA). The attributes appeared on a monitor in front of the panelists listing the attribute together with an unlabeled line scale anchored at the extremes. Panelists used a mouse click to locate a point on the line that indicated their rating of the perceived strength of each attribute.

1.5 Data Analysis

The data from individual panelists were screened for the ability to reproducibly differentiate the products on each attribute. Analysis of variance was used to identify the attributes that provided some discriminating power between the samples. Each panelist's scores were averaged over the entire panel to get a single value for each attribute-by-product combination.

Figure 6:
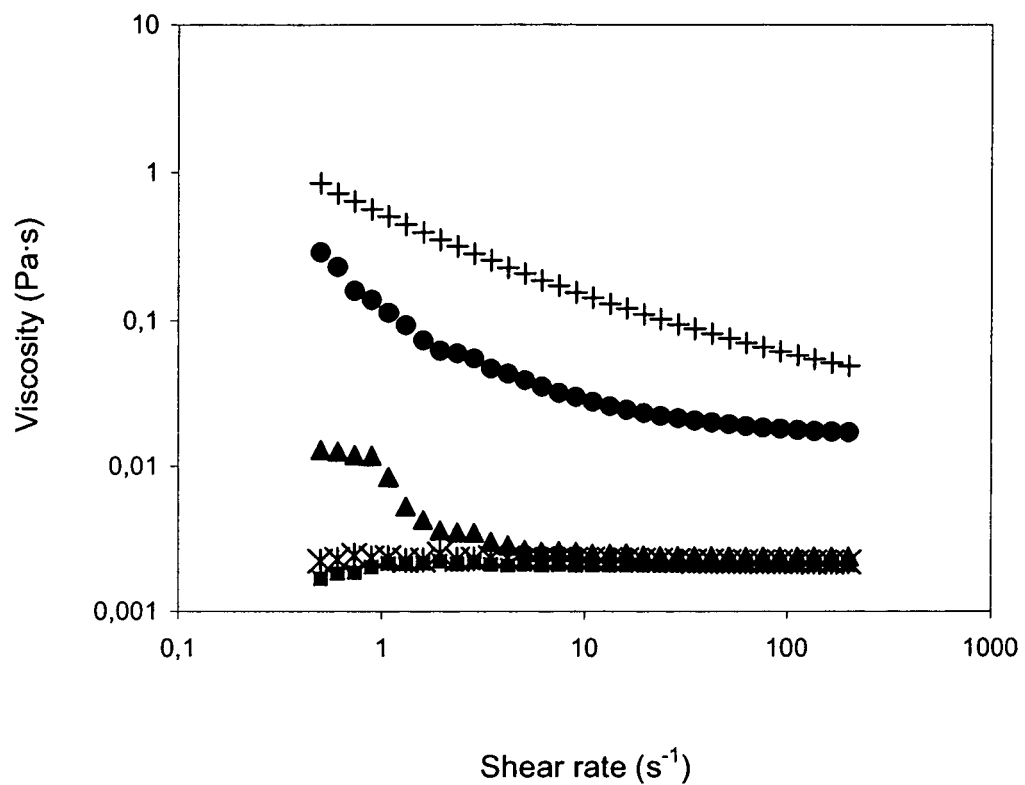
FIG. 6 is a graph showing the flow curves of the dairy emulsions with varying fat content: fat free skim milk (■), 2% reduced fat milk (*), whole milk (▲), half & half (●) and heavy cream (+)

Rheological analysis was performed in triplicate for each sample. The average shear stress was calculated as the slope of the shear stress against shear rate for shear rates between from $10 \text{ s}^{-1}$ to $100 \text{ s}^{-1}$. The average viscosity was calculated for shear rates between from $10 \text{ s}^{-1}$ to $100 \text{ s}^{-1}$ (FIG. 6). Linear regression (S-Plus 7.0 Insightful Corp, Seattle, Wash.) was used to relate these average shear stress and viscosity values to the average sensory values.

Tribological analysis was performed by measuring each sample four times using the above-described tribology device of the present invention. These four curves were averaged to get a single curve for each sample. The Matlab PLS Toolbox (Eigenvector Research Inc, Wenatchee, Wash.) was used to perform principal components analysis on these averaged data. The data were auto-scaled as a preprocessing step. Linear regression (S-Plus 7.0 Insightful Corp, Seattle, Wash.) was used to relate the principal component scores of the instrumental data and the average sensory attribute values.

2. Results 2.1 Principal of the Used Tribology Device

The used tribology device equipped with a ball-on-three-plates measuring geometry allows to accurately measure friction factor ($\mu$) and flow regimes as a function of sliding speed. A good lubricant, for example oil, results in a very low friction coefficient while measurements without lubricant, for example dry/dry contact area, shows a very high friction coefficient value. Since tribology measures the friction of materials, it allows the determination of additional physical properties which cannot be obtained only with viscosity measurements, i.e. by measuring shear stress/shear rate or oscillation parameters ("bulk rheology").

2.2 Sensory Results

Figure 5:
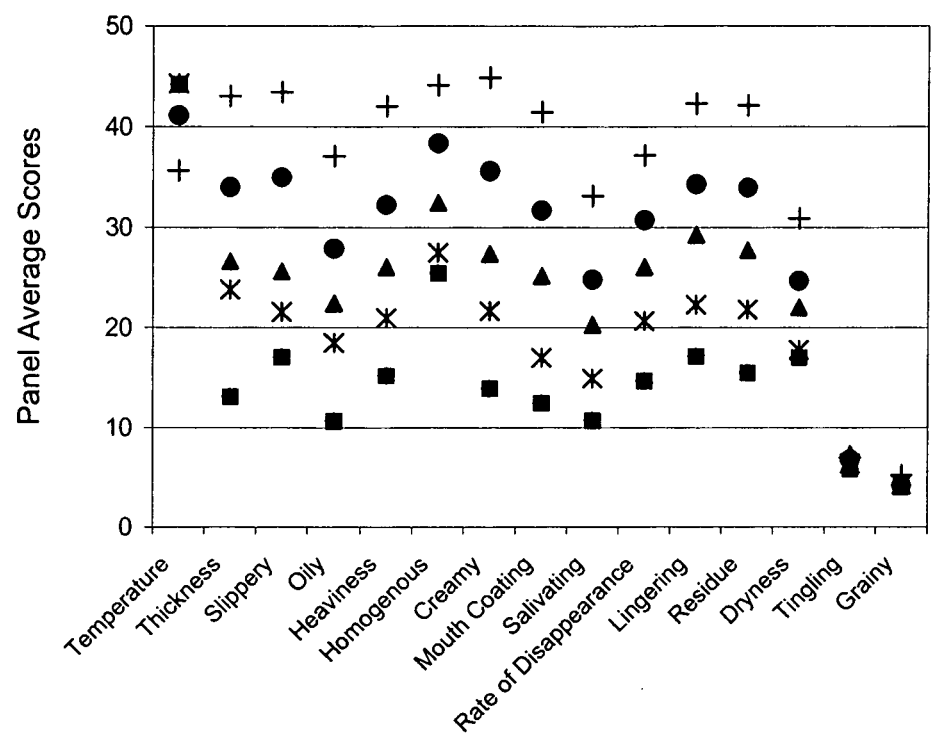
FIG. 5 is a chart showing the sensory panel average scores for each attribute of fat free skim milk (□), 2% reduced fat milk (*), whole milk (▲), half & half (●) and heavy cream (+)

The mouthfeel descriptors generated by the panel are summarized in Table 3 shown above. FIG. 5 shows the score of each attribute for each dairy sample. Note that most attributes show an ordering that follows the fat content of the products. This was consistent with the general expectation that higher fat tends to increase the overall mouthfeel intensity of most products. The overall ANOVA (analysis of variance) showed a significant ($p<0.01$) difference between the samples for all attributes with the exception of "grainy" and "tingling".

2.3 Instrumental Results

The flow curves depicted in FIG. 6 show the viscosity of each dairy sample as a function of shear rate. The low fat products, fat free milk, 2% reduced fat milk and the whole milk, show very little differences in viscosity at this shear rate. Only the half & half and the heavy cream appear to have distinguishably different viscosities across the flow profile. Fluid dairy emulsions are fairly Newtonian, however when stabilized with hydrocolloids, such as polysorbate 80 and carrageenan stabilized heavy whipping cream sample, the solutions are extremely shear thinning with low concentrations of hydrocolloids resulting in relatively high viscosities.

Using bulk rheological parameters alone, we can clearly see that there is no major distinction between the samples in terms of mouthfeel, especially not for those samples with a fairly low fat content. In fact, if we were to use the apparent viscosity of the dairy emulsion at a shear rate $50\,s^{-1}$, we could assume there is no difference in the mouthfeel of these samples. However the sensory panel clearly picked up significant differences in the perception of "creaminess" and "thickness" in these samples (refer to FIG. 5). Therefore, it is believed that rheology only gives part of the picture, when assessing mouthfeel. In order to better understand mouthfeel, it is required to look at complimentary methods, e.g. tribology, to better understand the ramification of ingredient choice on mouthfeel.

Figure 7:
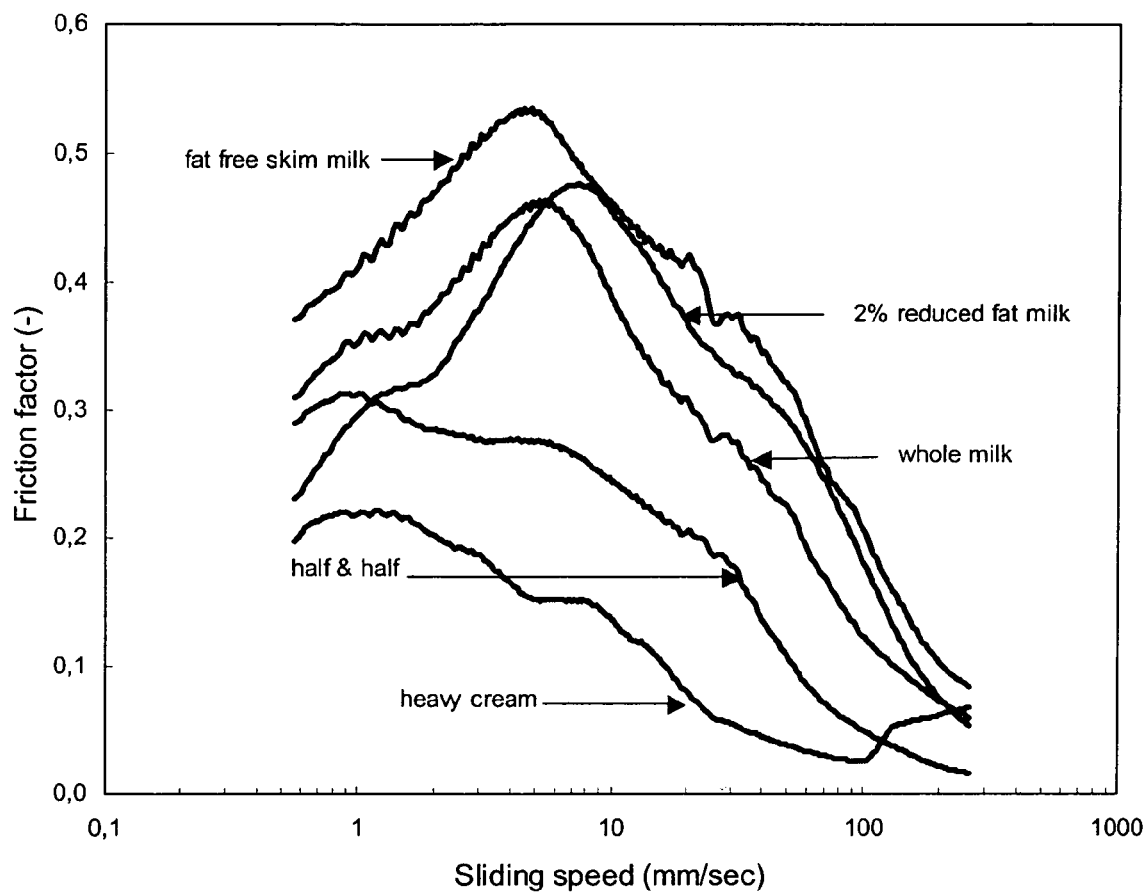
FIG. 7 is a graph showing Stribeck curves of friction factors versus sliding speed for fat free skim milk, 2% reduced fat milk, whole milk, half & half and heavy cream.

When assessing the friction and lubrication properties of the tested dairy emulsions, we can clearly discriminate between samples, even those, that have the same apparent bulk rheological properties (refer to FIG. 7). Fat free milk, 2% milk, and whole milk show a reduction in the friction coefficient at a sliding speed above 5 mm/s. This suggests that at low sliding speeds the sample is excluded from the contact-measuring surface between the ball and the three thermoplastic elastomer plates of the used tribology device and does not act as a lubricating agent. As the sliding speed increases the sample is adsorbed into the contact-measuring surface and becomes a more effective lubricating agent.

2.4 Correlation Models of Instrumental Properties and Sensory Attributes

Figure 8:
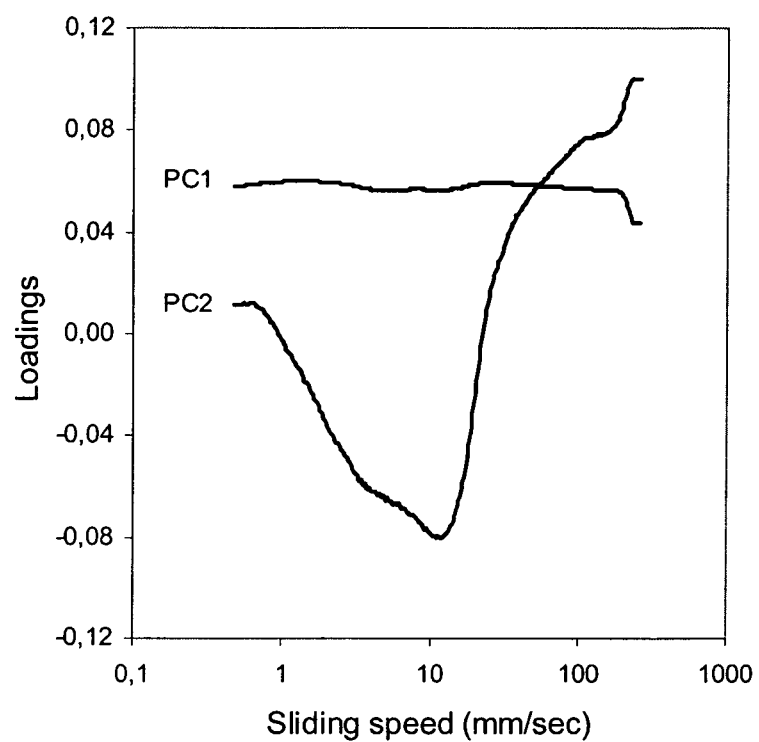
FIG. 8 is a PCA loading plot from the first two principal components (PC1 and PC2) which explain 91% and 6% of the variability, respectively.

The loadings plot shown in FIG. 8, derived from PCA (principal component analysis) of the tribology data, show that the first latent variable was, as expected, essentially an average over the sliding speeds. This indicates that the boundary to the mixed regimes of lubrication of the emulsions appear to be associated with the perception of certain mouthfeel attributes.

Figure 9:
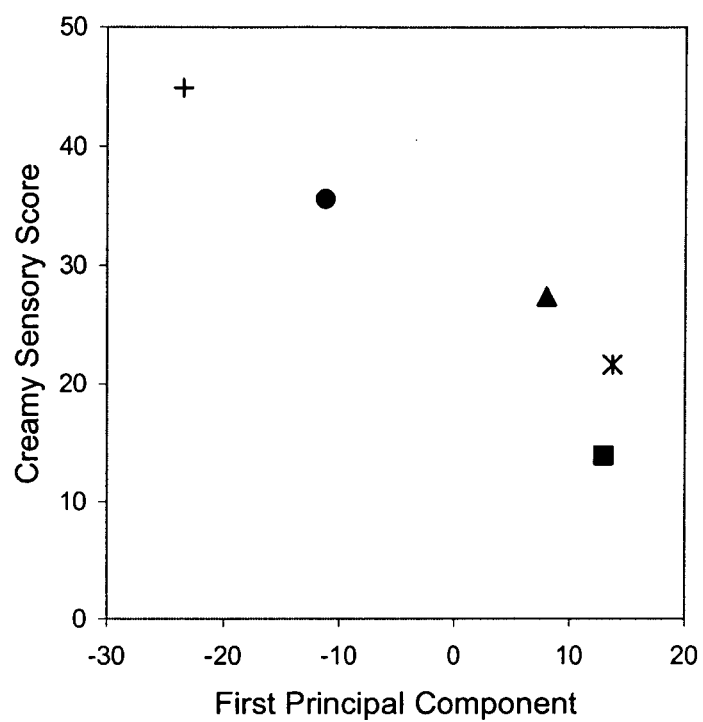
FIG. 9 is a plot showing the correlation between the sensory panel average scores for "creamy" and the scores from the first principal component for fat free skim milk (■), 2% reduced fat milk (*), whole milk (▲), half & half (●) and heavy cream (+)
Figure 10:
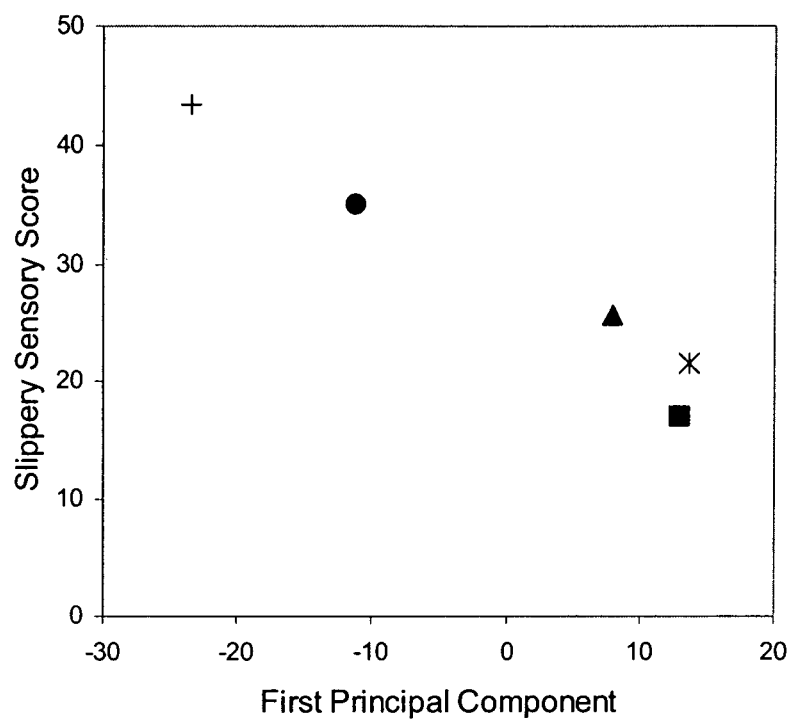
FIG. 10 is a plot showing the correlation between the sensory panel average scores for "slippery" and the scores from the first principal component for fat free skim milk (■), 2% reduced fat milk (*), whole milk (▲), half & half (●) and heavy cream (+)

The correlations between the scores of the first principal component of the tribological data and the sensory scores was statistically significant ($p<0.05$) for all attributes except "tingly" and "grainy". The plots shown in FIG. 9 and FIG. 10 are examples of the relationship between the tribological and sensory measures of "creamy" ($R^2=90\%$; slope=−0.7; intercept=28.7) and "slippery" ($R^2=96\%$; slope=−0.6; intercept=28.5).

Figure 11:
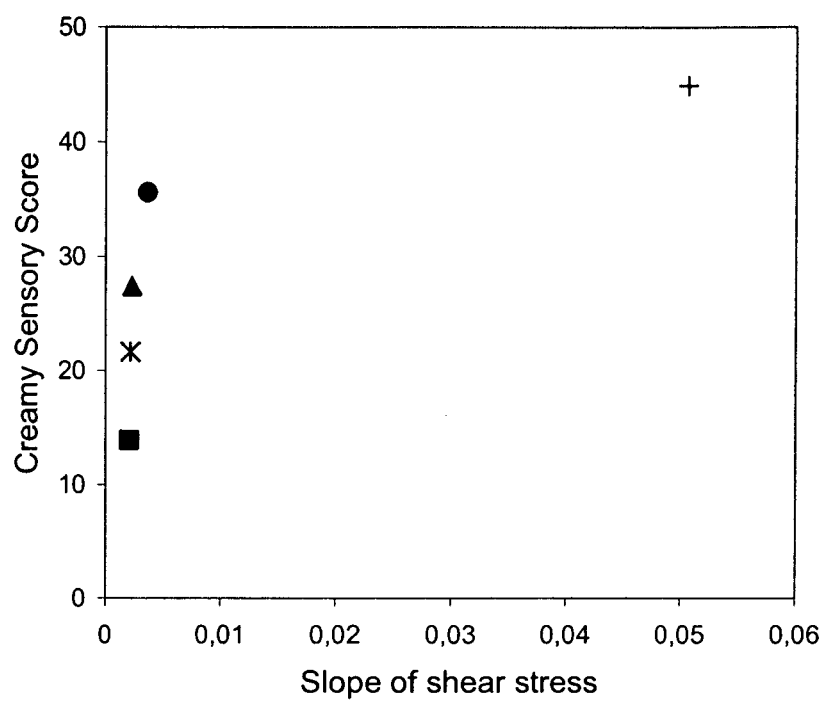
FIG. 11 is a plot showing the correlation between the sensory panel average scores for "creamy" and the slope of the shear stress curve for shear rates between 10 and 100 s$^{-1}$ for fat free skim milk (■), 2% reduced fat milk (*), whole milk (▲), half & half (●) and heavy cream (+)

In contrast, the relationship between the rheological measurements and sensory scores was statistically significant ($p<0.05$) only for the attributes "temperature" and "grainy". The plot shown in FIG. 11 is typical of the lack of relationship between the rheological and sensory variables "creamy" ($R^2=60\%$; slope=430.5; intercept=23.4).

These data indicate that the perception of the sensory attributes, especially "slipperiness" and "creaminess" could, at least in part, be predominately related to the lubricity of the food or beverage and that by tribological measurements using the novel tribology device of the present invention.

2.5 Conclusions

The above-discussed results, obtained by using a novel tribology device of the present invention, show that the friction and lubrications properties of fluid dairy emulsions are involved in the human sensory perception of "slippery" and "creaminess". Models, derived from the data appear to be capable of predicting these human sensory attributes. Therefore, tribology seems to be a valuable tool in assessing the mouthfeel properties associated with food systems or their components. This tool opens up the promising possibility for food developers to optimize the mouthfeel of fluid foods and beverages in a simpler and more cost-efficient manner.

Example 3

Correlation of Chocolate Mouthfeel Perception with Lubricity

The aim of this study was to assess the influence of lubricity, using a novel tribology instrument, and bulk rheological properties, along with the effect of composition and physical properties, such as melting transitions and particle size distribution, on the mouthfeel characteristics of various chocolate products.

The ability to assess mouthfeel attributes using instrumental techniques would greatly benefit the chocolate industry since sensory panels are time consuming and susceptible to a large range of variations. Chocolate samples with different particle size distribution, compositions and melting profiles were studied by dynamic shear rheology, tribology, and differential scanning calorimetry (DSC). The tribological and rheological properties were compared to quantitative descriptive analysis of the mouthfeel attributes of chocolate. Higher melting profile and higher average particle sizes evoked a significant reduction in the friction coefficient of the samples as a function of sliding speed. The impact of thermal transitions and particle size distributions of each chocolate sample was directly correlated to the frictional properties of the samples tested. Instrumental data was correlated to sensory attributes such as "smoothness", "creaminess", "mouth coating", and "grittiness". Overall the friction factor correlated well with these sensory attributes, giving product developers an additional tool to probe or screen for hedonic preferences.

1. Experimental Procedures 1.1 Material

Four commercially available chocolate samples were obtained from Fennema (a Cargill Company, Deventer, The Netherlands): DIP (ice dipping dark), CPW (compound chocolate coating white), CPD (compound chocolate coating dark), and ORG (chocolate organic) with various particle size distributions ranging from 27 μm to 40 μm and various melting point profiles ranging from 20° C. to 44.4° C. (Table 4).

The fat content was determined with the Soxhlet method. The moisture was determined with the method IOCCC n° 1:1952. The viscosities and yield values were determined by using the Casson method at 40° C. with Haake vT 550 with a spindle mv1. The fineness was determined by micrometry. The melting point was determined by DSC.

TABLE 4

Properties and composition of the model chocolates

| Product name | Fat content (%) | Fat type | Sugar content (%) | Moisture | Total cocoa (%) | Fineness (μm) |
|---|---|---|---|---|---|---|
| DIP | 66 | lauric | 25 | <1 | 10 | 27 |
| CPW | 37 | lauric | 45 | <1 | 0 | 39 |
| CPD | 40 | non-lauric | 39 | <1 | 11 | 40 |
| ORG | 35 | cacao | 43 | <1 | 56 | 40 |

| Product name | Melt point DSC (° C.) | Solid fat content % | Viscosity (mPa · s) | Yield value (Pa) |
|---|---|---|---|---|
| DIP | 23.12/29.65 | 98.93 ± 0.29 | 74.5 | 0.03 |
| CPW | 38.99 | 88.82 ± 2.53 | 591 | 0.33 |
| CPD | 38.87 | 76.12 ± 5.1 | 847 | 0.90 |
| ORG | 35.92 | 88.80 ± 1.65 | 7827 | 10.86 |

1.2 Rheological Measurements

The relationship between melt profile and particle size distribution on the yield point and flow properties of the Fennema chocolate samples was measured using a rheometer (Anton Paar MCR-301, Stuttgart, Germany). Small chunks of each chocolate sample were melted in Schott borosilicate glass bottles (500 ml) and conditioned in a water bath set to 50° C. and kept for 40 to 140 min, to ensure complete melting of the chocolate.

10 g of the melted chocolate were then transferred into a disposable aluminum pan that was pre-heated on the peltier-temperature unit to 40° C. The yield point and flow properties were determined after allowing the sample to equilibrate for 10 min and lowering the parallel plate configuration (PP25) onto the sample. Flow curves were is generated by increasing the shear rate of the instrument from 0.01 to 1000 s$^{-1}$ and plotting the viscosity as a function of shear rate in replicates of two.

1.3 Tribological Measurements

All tribology measurements were carried out on a MCR-301 rheometer (Anton Paar Stuttgart, Germany) using a tribology device of the present invention with a measuring system of the ball-on-three-plates geometry (FIGS. 1-3), which was temperature controlled by a peltier and hood temperature control system. Three elastomer strips made of a thermoplastic elastomer (TF6AAF material, available from KRAIBURG TPE GmbH, Waldkraiburg, Germany) were placed in the grooves on the plate of the tribology device.

Chunks of chocolate were then transferred in Schott borosilicate glass 500 ml bottles and conditioned in a water-bath set at 50° C. Melted chocolate were transferred to the tribology cell after 40 to 150 min at 50° C. (measured in n=4 replicates). The elastomer strips were conditioned at 40° C. (fan-assisted oven) 20 min prior to measurement.

The test temperature was set at 40° C. with an initial non-recording pre-shear of 0.4 mm/s for 10 min followed by recording the friction factor as a function of sliding speed (0.4 to 250 mm/s) at constant load of 3 N. The friction force $F_R$ is measured as a function of sliding speed. The friction factor μ was calculated as the ratio of friction force to normal force $F_R/F_N$.

1.4 Differential Scanning Calorimetric (DSC) Measurements

The melting behaviour of the chocolate samples was monitored using differential scanning calorimetry. Approximately 7 to 10 mg of chocolate sample were weighed into disposable aluminum pans and sealed hermetically. The pans were transferred to Q-1000 DSC (TA-Instruments, New Castle, Del.). A robotic arm placed the pans containing the chocolate samples in the sample cell of the DSC instrument and an empty pan was placed in the reference cell. The heat flow required to keep the two cells thermally balanced was then recorded as their temperature was increased from 5° C. to 80° C. at 5° C. per min.

The melting point of each chocolate was defined as the temperature at which a minimum occurred in the endothermic peaks. The solid fat content of each chocolate sample was calculated by determining the partial area under the melting peak at 40° C., which is equivalent to the percentage solid fat remaining at 40° C. and divided by the total area of the endothermic peak (until the base line was reached again).

1.5 Sensory Measurements

A trained quantitative descriptive analysis (QDA) panel was used to score the samples for mouthfeel attributes (see Table 5).

TABLE 5

| QDA mouthfeel attributes developed to describe the chocolate samples | |
|---|---|
| ATTRIBUTE | DESCRIPTION |
| MOUTHFEEL | |
| Initial: | |
| Hardness | Degree to which sample feels hard or firm when compressed against the roof of your mouth; soft - hard. |
| Rate of meltdown | Rate at which sample begins to melt or dissolve in your mouth; immediate - longer. |
| Pliability | Degree to which sample is pliable, or "squishable" and can be compressed without dissolving; rigid - pliable. |
| Manipulation required | Amount of manipulation required for sample to dissolve in mouth; low - high. |
| Middle: | |
| Slippery/Oily | Degree to which sample feels slippery, buttery, oily or silky; low - high |
| Chalky | Degree to which sample feels chalky in the mouth; low - high. |
| Waxy | Degree to which sample feels waxy or paraffin-like in the mouth; low - high |
| Well-Blended | Degree to which sample is smooth, well blended and consistent throughout; less - more. |
| Grainy | Degree to which sample feels gritty or grainy; smooth - grainy. |
| Coating | Degree to which sample coats mouth, tongue, back of throat, etc.; low - high. |
| Salivating | Degree to which sample causes salivation in the mouth; low - high. |
| Later: | |
| Overall rate of dissolving | Rate at which sample dissolves in mouth from initial to final stages; short - long. |
| Even melt | Degree to which residue or coating remains after sample removed from mouth; low - high. |

TABLE 5-continued

QDA mouthfeel attributes developed to describe the chocolate samples

| ATTRIBUTE | DESCRIPTION |
|---|---|
| AFTER EFFECTS (Sample removed from mouth) | |
| Residue remaining | Degree to which residue or coating remains after sample removed from mouth; low - high. |
| Dryness | Degree to which mouth feels dry after sample removed; low - high. |
| Astringent | Degree to which sample causes astringent feeling in mouth; low - high |

1.6 Data Analysis

Linear regression (S-Plus 7.0 Insightful Corp, Seattle, Wash.) was used to correlate yield stress and viscosity values to the average sensory values.

Tribological analysis was performed by measuring each sample four times using the above-described tribology device of the present invention. These four curves were averaged to get a single curve for each sample. The Matlab PLS Toolbox (Eigenvector Research Inc, Wenatchee, Wash.) was used to perform principal components analysis on these averaged data. The data were auto-scaled as a preprocessing step. Linear regression (S-Plus 7.0 Insightful Corp, Seattle, Wash.) was used to relate the principal component scores of the instrumental data and the average sensory attribute values.

2. Results 2.1 Sensory Results

The descriptors developed by the panel along with their definitions are shown in Table 4. The individual descriptors were broken out in different phases of the eating process from initial and middle to later and after effects. The initial attributes were mainly related to the initial feels of the chocolates and the sensation produced as they melted. The attributes seen in the middle phase of eating seemed to be a blend of those that could possibly be related to flow and viscosity such as "well-blended" as well as those that could be related to lubricity and friction such as "chalky" and "slippery/oily". The attributes in the later category seem to be related to the removal of the product from the mouth, such in preparation for swallowing, and the start of the perception of a residual or mouth coating. The attributes sensed as after effects had the potential to be related to the sensation of the residuals left but also to changes in the oral surfaces even after the product was no longer in the mouth.

Figure 12:
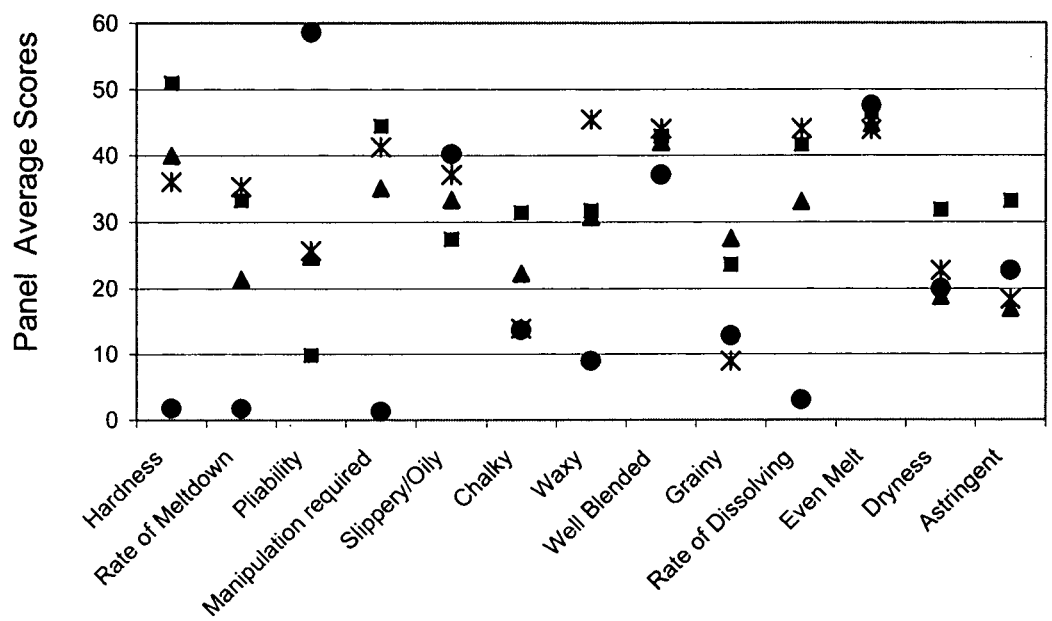
FIG. 12 is a plot showing the sensory panel average scores for each attribute of the chocolate samples ORG (■), CPD (*), CPW (▲), and DIP (●)

Ratings from 10 panelists were averaged together. FIG. 12 shows the product averages for all the attributes. The overall ANOVA (analysis of variance) showed a significant ($p<0.05$) difference between the samples for all attributes with the exception of "even melt".

Trends were seen across several of the attributes and appear to correlate with the composition and physical properties of the samples. For example, the fineness was significantly ($p<0.05$) correlated with the sensory attributes "hardness", "manipulation required", "well blended" and "rate of dissolving". The significant relationship between "fineness" and "hardness" ($R^2=92\%$; slope=3.2; intercept=−84.9) is driven primarily by the DIP sample. DIP with its low yield value, low viscosity, low melting point, low fines, high fat content, and low sugar content seemed to show low levels of most sensory descriptors except those ones that involve motion in the mouth, namely "pliability", "slippery/oily", "well blended", and "even melt". DIP did have the same levels of "astringent" and "dryness" as the other samples.

In general, "hardness", "rate of melt down", and "rate of dissolving" all appeared to increase with increases in viscosity, yield value, and fineness. "Pliability" showed the opposite behaviour of decreasing in intensity as viscosity; yield value, fineness, and total fat increased. Higher melting point seemed to correspond to increased intensity of "manipulation required" and "waxy" attributes and lower intensity of the "slippery/oily" attribute. An increase in solid fat content seemed to correspond to a decrease in "waxy" intensity.

2.2 Instrumental Results

Figure 13:
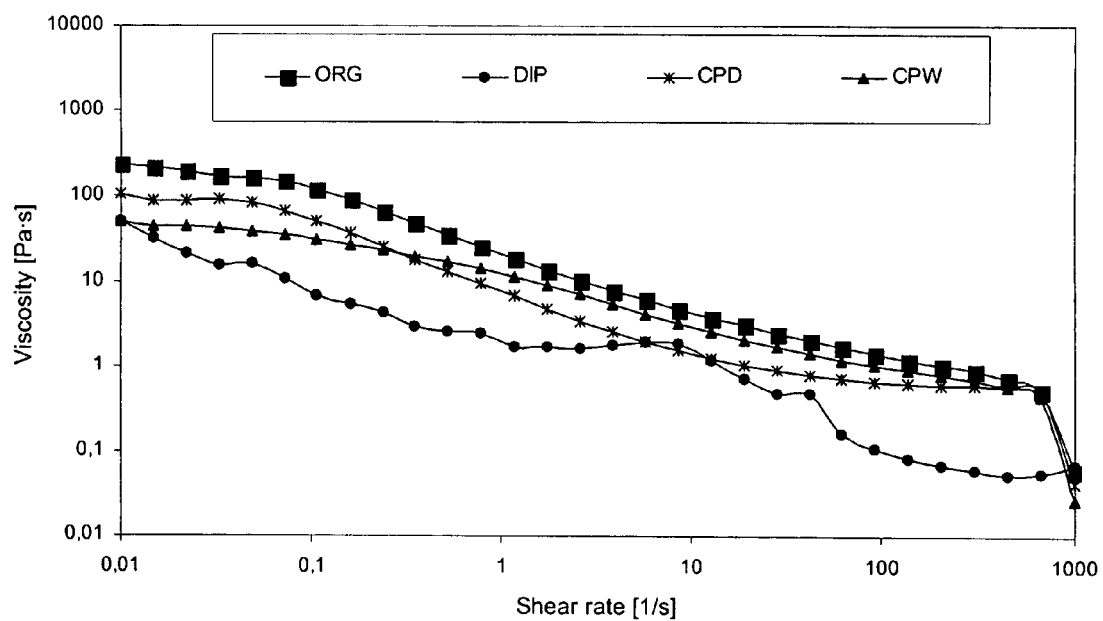
FIG. 13 is a graph showing viscosity as a function of shear rate of the chocolate samples ORG (■), CPD (*), CPW (▲), and DIP (●) with varying fat content, particle size distribution and melting point profiles.

Typical flow curves for the samples are shown in FIG. 13.

Figure 14:
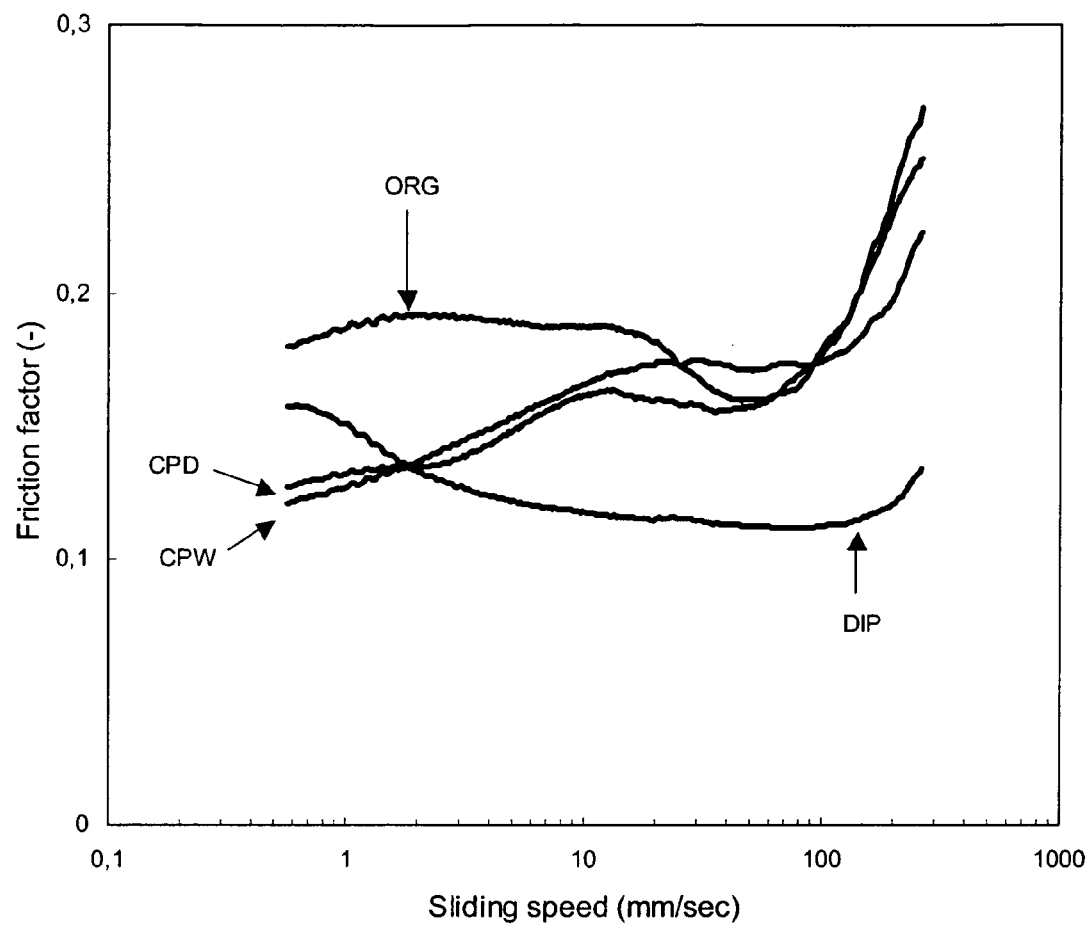
FIG. 14 is a graph showing Stribeck curves of friction factors versus sliding speed for ORG, CPD, CPW and DIP.

Typical Stribeck curves (friction factor as a function of sliding speed) are shown in FIG. 14, revealing that the samples exhibited very different tribology behaviour. The DIP sample showed a slight decrease in the friction factor over most of the sliding speeds. The high fat content of DIP results in low friction factor values over sliding speeds.

The CPD and CPW samples showed an initial increase in friction factor at the lower sliding speeds, followed by a plateau in friction factor at the medium sliding speeds from 10 mm/s to 100 mm/s after which the friction factor rapidly increased with sliding speed.

The ORG sample showed the highest starting friction factor (~0.2). The friction factor for this sample remained at this level up to a sliding speed of about 90 mm/s after which it rapidly increased.

The velocity dependence of the friction force is known to depend on the composition of the chocolate. Previous work showed a strong correlation of the chocolate's tribological properties with the particle size distribution and lecithin content (Lee et al. *J. M. Food Science* 67: 2712-2717 (2002)). However the variation in milk fat/cocoa butter ratio was found to have an insignificant effect on the tribological properties.

The presence of particles suspended in a continuous fat phase generally is known to result in two major changes in the lubrication properties, when comparing fat components to a system with suspended solid particles, e.g. chocolate: (1) an increase in viscosity and (2) the tribology device is subjected to abrasive wear (Lee et al., *Tribol. Lett.* 16: 239-249 (2004)). Therefore, it has been suggested that the steep increase in friction at higher sliding speeds could be the result of several possible modes of particle behaviour, which include accumulation at the inlet of the geometry, and starvation of the fat supply into the contact area (Lee et al. (2004); supra).

It was suggested that a strongly adsorbed hydrophobic monolayer is always present during sliding. The monolayer determines the contact angles and therefore will have a great influence on any interface induced physical properties displayed throughout the chocolate film, because of preferential accumulation of proteins and water or the lipid phase at the interface (Luengo et al. (1997); supra).

2.3 Correlation Models of Instrumental Properties and Sensory Attributes

Figure 15:
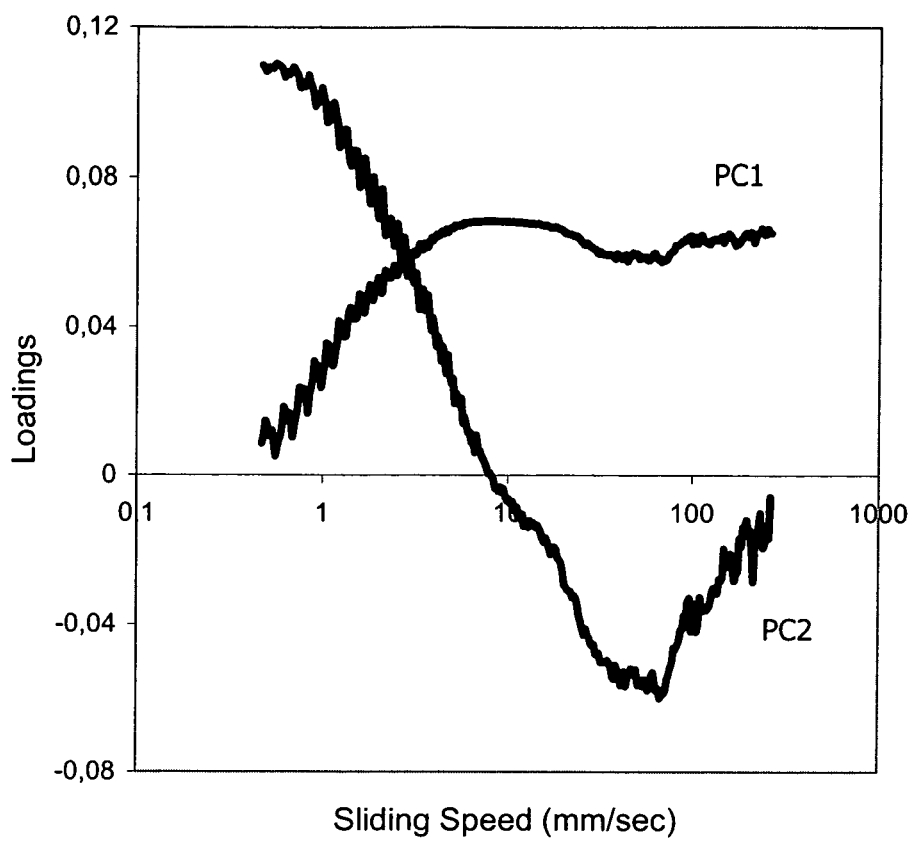
FIG. 15 is a PCA loading plot from the first two principal components PC1 and PC2 which explain 71% and 27% of the variability, respectively.

The first two principal components of the tribology data captured 71% and 27.18% of the variance for a total of 98.3%. The loading plot (FIG. 15), from PCA (principal component analysis) of the tribology data, showed that the first latent variable was essentially the average friction factor once the sliding speed had reached approximately 10 mm/s. The second principal component is a contrast of the friction factor at the low sliding speed and the high sliding speeds.

Figure 16:
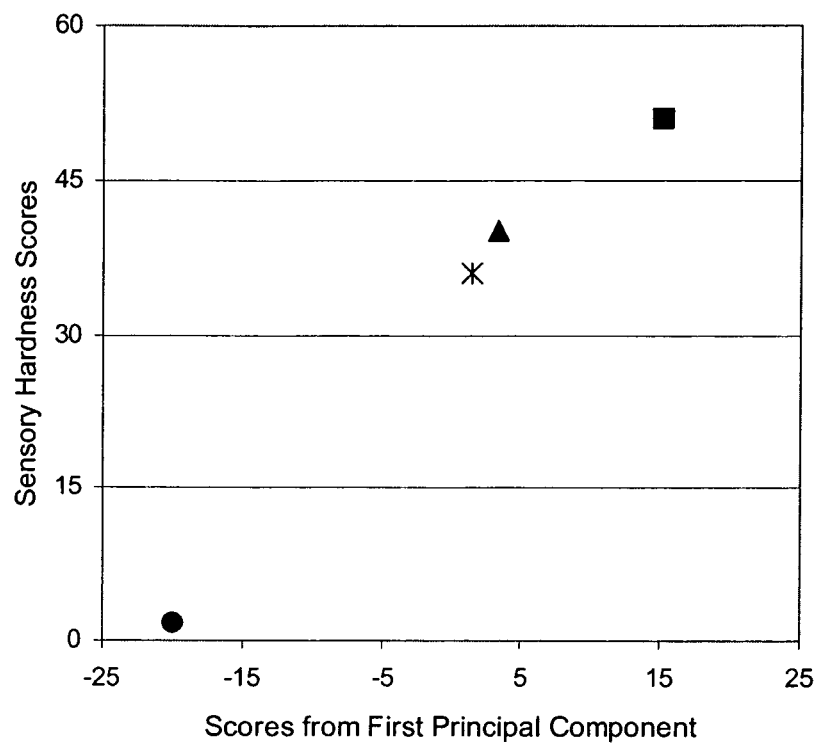
FIG. 16 is a plot showing the correlation between the sensory panel average scores for "hardness" and scores from the first principal component for ORG (■), CPD (*), CPW (▲) and DIP (●)
Figure 17:
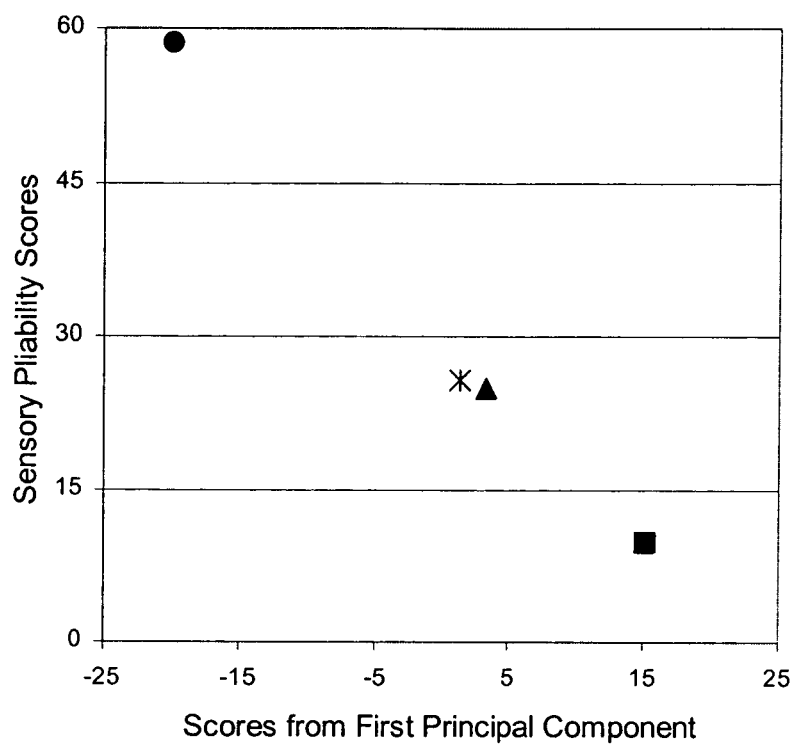
FIG. 17 is a plot showing the correlation between the sensory panel average scores for "pliability" and scores from the first principal component for ORG (■), CPD (*), CPW (▲) and DIP (●)

The relationship between the scores of the first principal component of the tribological data and the sensory scores was statistically significant ($p<0.05$) for the attributes "hardness" ($R^2=98\%$; slope=1.4; intercept=32.2) and "pliability" ($R^2=99\%$; slope=−1.4; intercept=29.7). The plots shown in FIG. 16 and FIG. 17 are examples of the relationship between the tribological data and sensory measures of "hardness" and "pliability".

"Hardness" is positively correlated with the scores of the first principal component of the tribological data. This seems to indicate that the lubricity of the mass of chocolate, as it first starts to melt and during melting in the mouth, is an important driver of these initial mouthfeel sensations. This was not expected since it was believed that most of the lubricating properties of the melted mass would be perceived much later in the eating process or perceived as after-effects.

Figure 18:
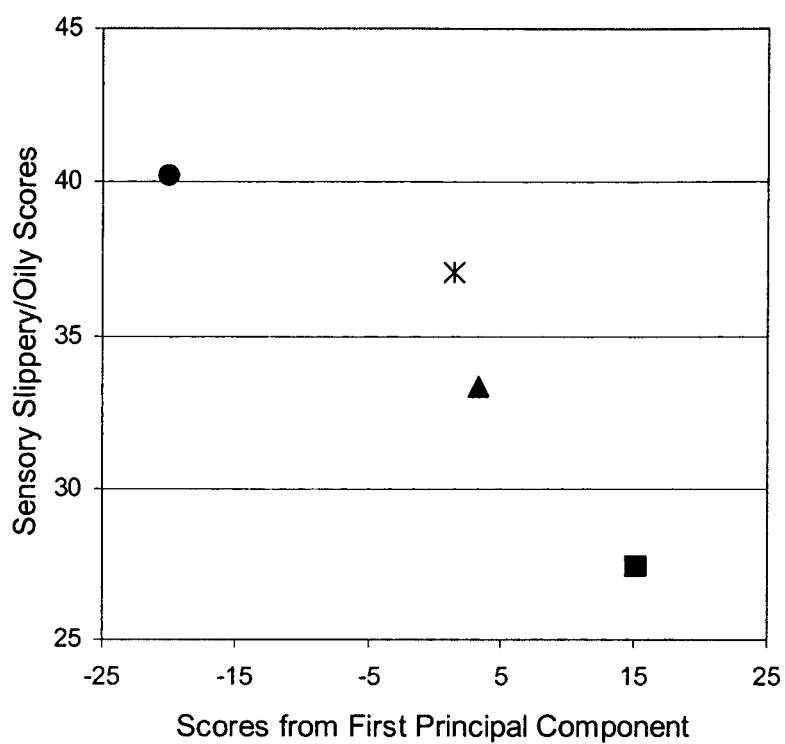
FIG. 18 is a plot showing the correlation between the sensory panel average scores for "slippery/oily" and scores from the first principal component for ORG (■), CPD (*), CPW (▲) and DIP (●)

The plot in FIG. 18 shows the relationship between the tribological data and "slippery/oily" ($R^2=85\%$; slope=−0.3; intercept=34.5). This relationship was only borderline significant ($p=0.08$) but supports the conclusion that tribology is related to the sensations of lubrication in the oral cavity.

Surprisingly, rheological measurements of yield and viscosity were only significantly correlated ($p<0.05$) with the sensory attribute "dryness". This shows that viscosity measurements alone do not adequately characterize the mouthfeel of chocolate samples.

2.4 Conclusions

The above-discussed results, obtained by using a novel tribology device of the present invention, show that the friction and lubrications properties of chocolate are involved in the human sensory perception of "hardness" and/or "pliability" and "slippery/oil". Models, derived from the data appear to be capable of predicting these human sensory attributes. Therefore, tribological measurements represent a complementary instrumental approach to rheology in order to better assess mouthfeel properties of various food and beverages. Tribology is assumed to be a valuable tool in assessing the mouthfeel properties associated with food systems or their components. This tool therefore will allow food developers to optimize the mouthfeel of food and beverage, including transitional semi-solids like chocolate, that are governed by complex rheological and tribological properties, in a simple, reproducible and cost-efficient manner.

Example 4

Differentiation of "Body" in Sweetener Solutions

The aim of this study was to assess the role of lubricity by using the novel tribology device of the invention, in the mouthfeel sensations, in particular in the "body" attributes of sweetener solutions sweetened with 10% sugar and the high intense sweetener aspartame (present in an amount to achieve equal sweetness of 10% sucrose).

Sweeteners are one group of food ingredients that are known to impart mouthfeel or body to beverages. Aspartame and other high intense sweeteners, such as acesulfame K, saccharin, cyclamate, and sucralose are widely used in "0" calorie and light beverages. However, diet beverages including such high intense sweeteners are known to be distinguished differently by consumers from full calorie beverages with respect to body and mouthfeel attributes, a fact which is well known in the beverage industry. While sensory thresholds of mouthfeel and body attributes for beverages that are sweetened with sucrose and high-fructose corn syrup (HFCS) have been found, researchers failed to show that they were strongly related to the viscosity produced by these sweeteners in the beverages tested (Kappes, S. M. et al. 2006, Food Science, 71(9): S597-S602).

Since most beverages and fluid food products are very low in viscosity and have no measurable yield stress, the present inventors proposed that these mouthfeel and body attributes must be related to other forces in the mouth, such as lubrication, that lead to the sensations of mouthfeel and body in these products. To further illustrate the differentiation ability of the tribology device of the present invention, 10% (w/w) solutions of polydextrose and of Fibersol 2 were included. Both soluble dietary fibres are used as sucrose replacement in conjunction with high intense sweeteners in beverages.

1. Experimental Procedures

1.1 Material

10% (w/w) solutions of Fibersol 2 (Matsutani, Clinton, Iowa, USA) and polydextrose (Danisco, New Century, USA), respectively, were freshly prepared using Evian water+0.06% (w/w) aspartame to obtain 10% SEV. An aspartame 0.06% (w/w) solution and a 10% (w/w) sucrose solution were taken as 10% SEV reference solutions.

1.2 Rheological Measurements

Apparent viscosities of the solutions were measured using the constant stress rheometer (Anton Paar MCR-300, Stuttgart, Germany) using the cylindrical configuration (CC24). The samples were equilibrated at 20° C. in a temperature-controlled room for 1 h. After a pre-shear step (from 1 to 10 s$^{-1}$) of 2 min, the samples were placed in the measurement cell at 20° C., and flow curves were generated by increasing the shear rate from 10 s$^{-1}$ to 100 s$^{-1}$.

1.3 Tribological Measurements

All tribology measurements were carried out on a MCR-301 rheometer (Anton Paar, Stuttgart, Del.) using a tribology device of the present invention with a measuring system of the ball-on-three-plates geometry (FIGS. 1-3), which was temperature controlled by a peltier and hood temperature control system. Three elastomer strips made of a thermoplastic elastomer (TF6AAF material, available from KRAIBURG TPE GmbH, Waldkraiburg, Germany) were placed in the slots on the plate of the tribology device.

The test temperature was set at 20° C. with an initial non-recording pre-shear of 0.4 mm/s for 10 min followed by recording the friction coefficient as a function of sliding speed (0.4 to 250 mm/s) at constant load of 3 N. The friction force $F_R$ is measured as a function of sliding speed. The friction factor or coefficient µ was calculated as the ratio of friction force to normal force $F_R/F_N$.

2. Results

2.1 Instrumental Results

Figure 19:
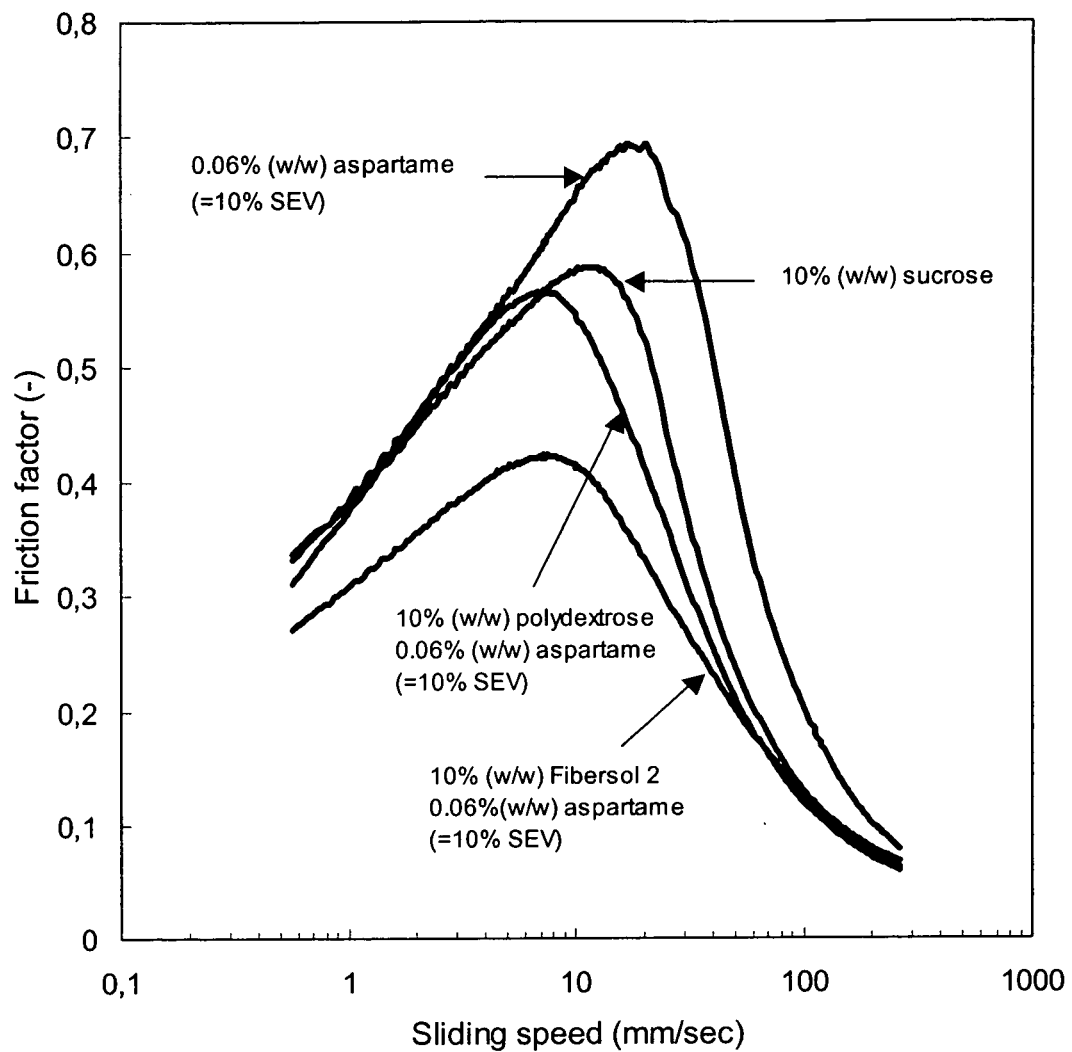
FIG. 19 is a graph showing the Stribeck curves of 10% (w/w) sucrose and soluble dietary fibre solutions in comparison to a 0.06% (w/w) aspartame solution.

Typical Stribeck curves (friction factor as a function of sliding speed) are shown in FIG. 19. The samples exhibited very different tribology behaviour in that the aspartame solution shows a much higher friction factor than the sucrose solution. The soluble dietary fibres, especially Fibersol 2, exhibited an even more pronounced lubrication effect compared to the sucrose solution.

In contrast, the average viscosity values of the sample solutions (0.06% (w/w) aspartame: 1.11 mPa·s; 10% (w/w)

sucrose: 1.48 mPa·s; 10% (w/w) polydextrose+0.06% (w/w) aspartame: 1.61 mPa·s; 10% (w/w) Fibersol 2+0.06% (w/w) aspartame: 1.70 mPa·s) are very close to water (1.003 mP·s at 20° C.), indicating that bulk rheology measurements of apparent viscosities are clearly insufficient to differentiate the influence of a particular sweetener type (or soluble fiber type) on mouthfeel.

2.2 Conclusions

The above results show that tribology is a valuable tool to differentiate sweet solutions or sweetened beverages with respect to mouthfeel differences. This tool opens promising possibilities for food developers to optimize mouthfeel of fluid foods and beverages in a simple and cost-efficient manner.

Example 5

Identification of a Composition Suitable for Replacing High Caloric Sweeteners in Beverage The aim of this study was to identify with tribology a iso-sweet, iso-viscous ingredient system blend, which is a suitable low or "0" caloric substitute of sucrose in beverages and the like, using the tribology device of the invention.

1. Experimental Procedures 1.1 Material

Different blends of soluble fibers were tested using the tribology device according to the invention in order to find an innovative combination, which is a suitable substitute of sucrose in beverages. For this particular example two soluble fibers have been selected: Benefiber (Novartis, Basel, Switzerland) and Sunfiber R (Tayo, Yokkaishi Mie, Japan).

1.2 Rheological and Tribological Measurements

Rheological procedures and tribological procedures are identical to the one of Example 4, except that for the tribology measurements another elastomer substrate was used (TF5EFD material, available from KRAIBURG TPE GmbH, Waldkraiburg, Germany).

2. Results 2.1 Instrumental Results

Aspartame 0.06% (w/w) and 10% (w/w) sucrose solution were taken as 10% SEV reference solutions. The average viscosity at 20° C. of n=6 replicates was 1.11±0.10 mPa·s and 1.48±0.08 mPa·s, respectively.

Figure 20:
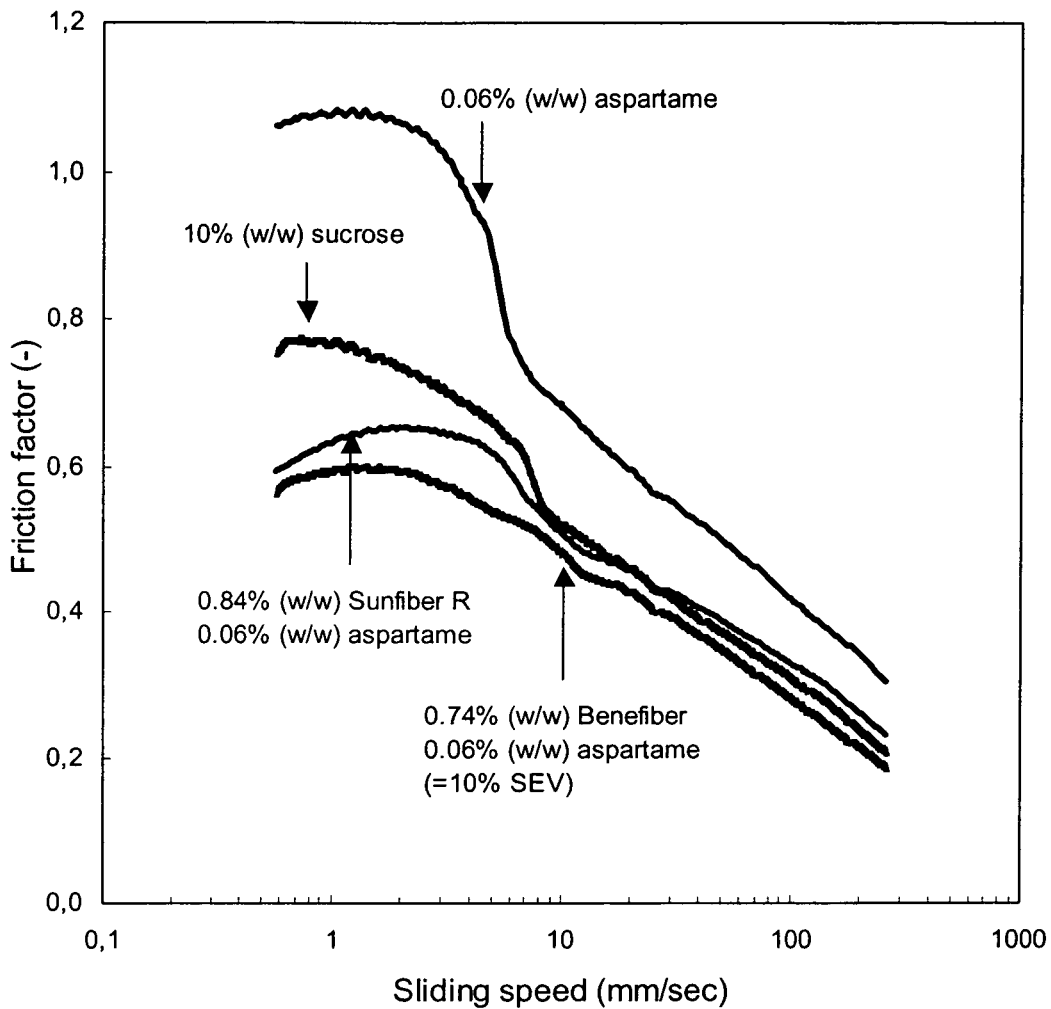
FIG. 20 is a graph showing the Stribeck curves of 10% (w/w) sucrose solutions in comparison to a 0.06% (w/w) aspartame solution and iso-sweet+iso-viscous soluble fiber solutions.

Typical Stribeck curves were determined using both soluble fiber types at concentrations to obtain iso-viscous and iso-sweet solutions compared to a 10% (w/w) sucrose solution, as shown in FIG. 20.

The blend of 0.06% (w/w) aspartame and 0.74% (w/w) Benefiber (viscosity: 1.44 mPa·s) or the blend of 0.06% (w/w) aspartame and 0.84% (w/w) Sunfiber R (viscosity: 1.43 mPa·s), although close to the sucrose profile, exhibit still a better lubrication compared to the 10% (w/w) sucrose solution (viscosity: 1.48 mPa·s) and much better lubrication than the 0.06% (w/w) aspartame solution (viscosity: 1.11 mPa·s).

This confirms again that viscosity measurements alone do not adequately characterize the mouthfeel of sweetener solutions and beverages.

2.2 Conclusion

Tribology opens promising possibilities for food developers to identify and formulate low or "0" calorie ingredient systems to create similar mouthfeel to standard high caloric sucrose solutions in a simple and cost-efficient manner.

Example 6

Differentiation of Dairy Drinks

This example illustrates the differentiation of dairy drinks by tribology.

1. Experimental Procedures 1.1 Material

Samples of skim milk and whole milk were purchased at a local supermarket. A dilution series was made consisting of 0, 25, 50, 75, and 100% whole milk.

1.2 Tribology Measurements

All tribology measurements were carried out on a MCR-301 rheometer (Anton Paar USA, Ashland, Va., USA) using a newly developed tribology cell (Anton Paar Germany GmbH, Ostfildern, Germany). The test temperature was set at 20° C. with an initial non-recording pre-shear of 0.4 mm/s for 5 min followed by recording the friction coefficient as a function of sliding speed (0.4 to 250 mm/s) at constant load of 3 N using the TF5 EFD cork on TF5 EFD (KRAIBURG TPE GmbH, Waldkraiburg, Germany) strips. The friction force $F_R$ is measured as a function of sliding speed. The software calculates the ratio of friction force to normal force $F_R/F_N$, which is called the friction factor or coefficient μ.

Each dairy sample was analyzed in triplicate using the tribology device. The three runs were averaged and the average friction factor as a function of sliding speed was recorded.

2. Results

Figure 21:
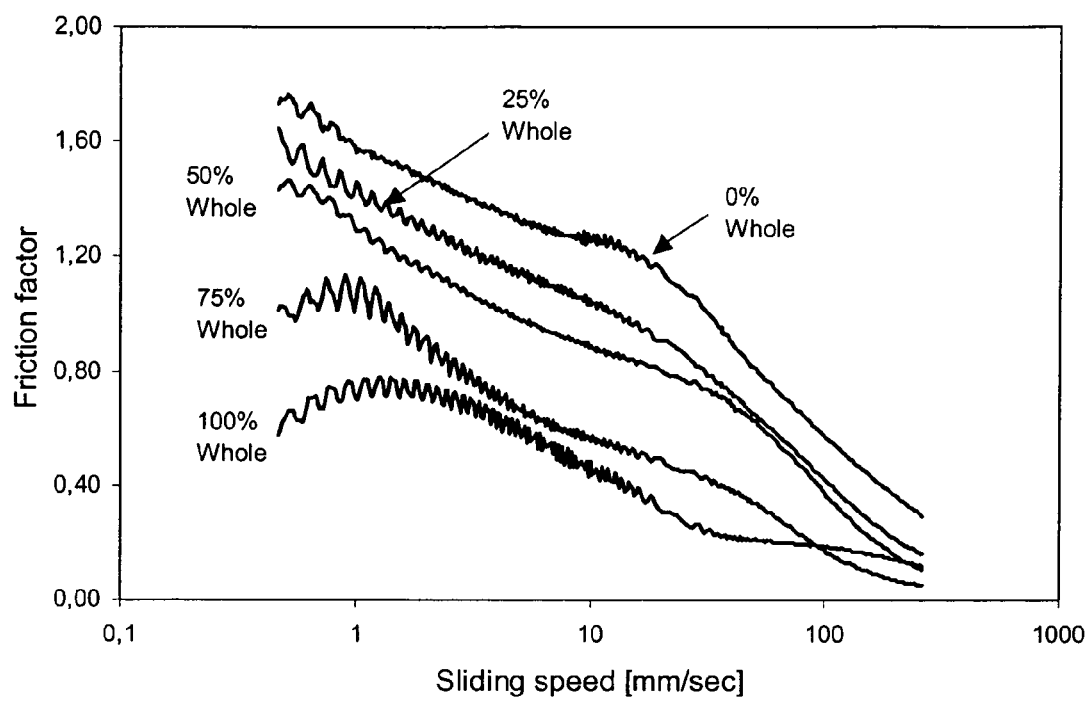
FIG. 21 is a graph showing the Stribeck curves of 0%, 25%, 50%, 75%, and 100% whole milk.

The results are show in FIG. 21. The plot of average friction factor at each sliding speed shows differentiation between the dairy samples.

Example 7

Differentiation of Chocolates

This example illustrates the differentiation of chocolates by tribology.

1. Experimental Procedures

Chunks of chocolate were transferred in Schott borosilicate glass 500 ml bottles. Schott borosilicate glass was conditioned in a water-bath set at 50° C. Melted chocolate were transferred to the tribology cell after 40 to 150 min at 50° C. (measured in n=4 replicates). The elastomer strips (made of HTF8654/94, available from KRAIBURG TPE GmbH, Germany) were conditioned at 40° C. (fan-assisted oven) 20 min prior to measurement.

The test temperature was set at 40° C. with an initial non-recording pre-shear of 0.4 mm/s for 10 min, followed by recording the friction factor as a function of sliding speed (0.4 to 250 mm/s) at constant load of 3 N. The friction force $F_R$ is measured as a function of sliding speed. The friction factor μ was calculated as the ratio of friction force to normal force $F_R/F_N$.

Chocolate samples were measured using the tribometer. The Cacao Donker sample as was measured three times, and all other samples were measured four times.

2. Results

Figure 22:
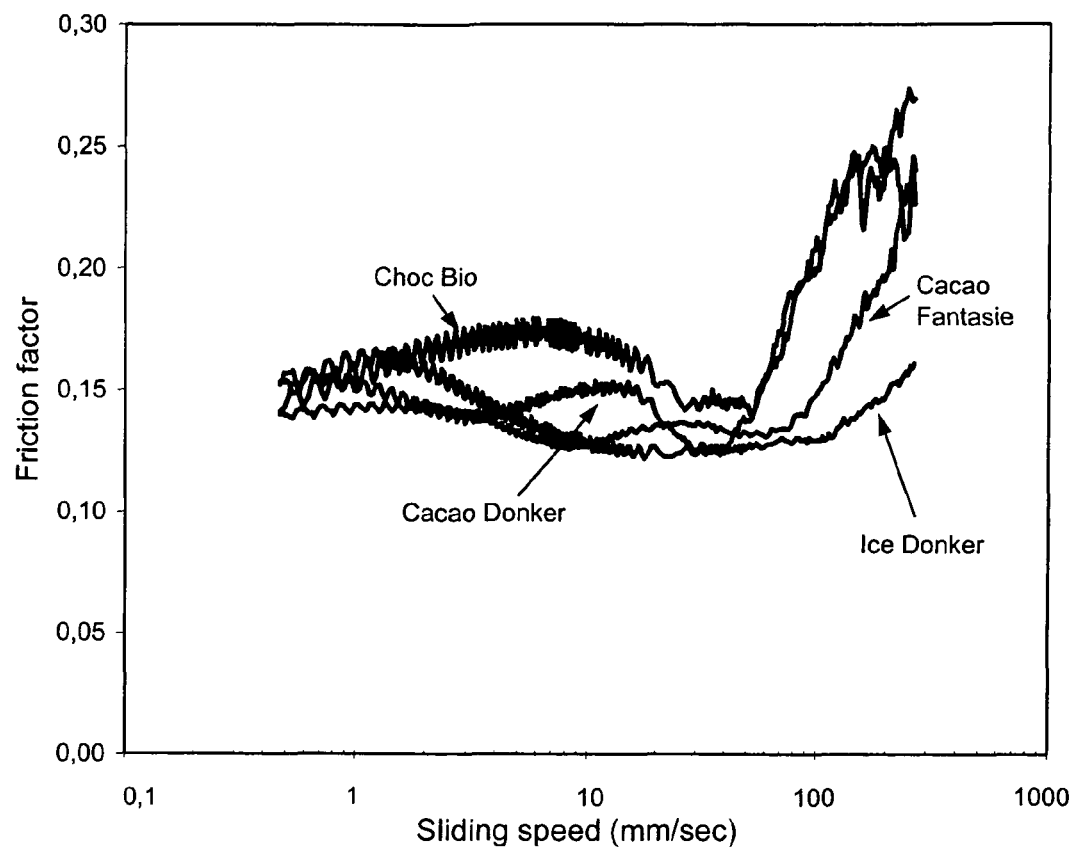
FIG. 22 is a graph showing the Stribeck curves of different chocolate samples.

The measured averaged friction factors as a function of sliding speed is shown in FIG. 22. As seen in FIG. 22, the different chocolate samples are well differentiated.

Example 8

Differentiation of Emulsions and Correlation of Friction Factor with Creaminess

This example illustrates an embodiment of a method of the present invention.

1. Experimental Procedures
1.1 Material
Starting Materials

Spray-dried Na caseinate was from Rovita (FN5S). Anhydrous milk fat (melting point 30° C. to 32° C.) was from Campina Milk Fat Products N.V. Spray-dried maltodextrin (1DE), xanthan gum and guar gum were from Cargill.
Emulsion Preparation and Droplet Size Measurement Na caseinate was dissolved in demineralised water at room temperature. The aqueous phase (4 wt. % protein, pH 6.8) and the fat were mixed with an Ultra-Turrax (speed 1-2 for 5 min) and heated in a water-bath at 50° C. for 40 min.

Fat-in-water emulsions (30 vol. %, 2.8 wt. % Na caseinate) were prepared at 50° C. using a Rannie homogenizer operating at 350 bar. The hydrocolloid (maltodextrin or xanthan) was dissolved in demineralised water at room temperature to a solution of known concentration. Fat-in-water emulsions (30 vol. %) and hydrocolloid solution were mixed by gentle stirring in order to adjust the fat content (20 vol. % and 5 vol. %) and the viscosity.

The emulsion droplet-size distribution was evaluated with a Sympatec laser light-scattering analyser (with a Quixel wet dispersing system). The average droplet size of the 30 vol. % emulsion was 0.86 μm and there was no change in the average droplet size when diluted to achieve 20 vol. % and 5 vol. % fat-in-water emulsions.

1.2 Rheological Measurements

Steady state viscosities versus shear rate (log ramp from 1 to 100 $s^{-1}$) were measured using Haake Rheostress 1 concentric cylinder Z41 geometry (20° C., temperature equilibration time=5 min). Similar results were obtained using the MCR300 Anton Paar rheometer with cylindrical geometry CC24 at 20° C.

1.3 Tribological Measurements

The thermoplastic elastomer TF6 AAF (Kraiburg PTE, Germany) was cut into 1.8×0.6×0.2 cm strips. Prior and after test, the strips were cleaned with diluted soap, rinced thoroughly with tap water and dried with tissue paper by blotting. The upper ball-shaped element was made of steel.

The tests were performed in duplicate or triplicate at random at a temperature of 20° C. and a normal force 3 N, and using the following conditions:
(i) non-recording pre-shear (speed 1 $min^{-1}$ or sliding speed 0.47 mm/s) for 5 min;
(ii) recording shear (speed 1-560 $min^{-1}$ or sliding speed 0.47-250 mm/s) (300 measuring points, for 587 s).

1.4 Sensory Measurements

Fat-in-water emulsions of known fat content and viscosity were assessed in duplicate as described by Akhtar et al. (2005). Panel members were asked to rate creaminess on a scale of 1 to 10, where 10 corresponds to the intensity highest rating.

1.5 Data Analysis

PCA was performed with CAMO Unscrambler software.

2. Results

Figure 23:
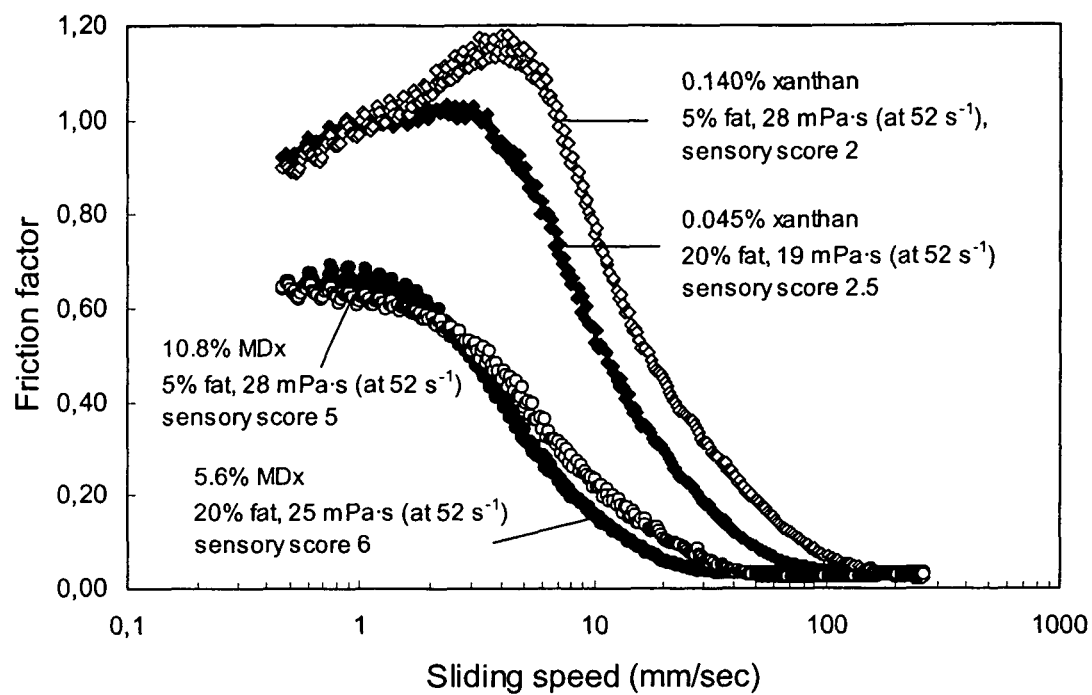
FIG. 23 is a graph showing the Stribeck curves of maltodextrin and xanthan containing isoviscous solutions.

With a background of identical droplet size distribution, 20 vol. % and 5 vol. % fat-in-water emulsions of ~70 mPa·s and ~20 mPa·s apparent viscosities (at 52 $s^{-1}$) were characterised by tribology (see FIG. 23) and sensorial analysis. The results are shown in Table 6.

TABLE 6

| Fat (vol. %) in emulsion | Hydrocolloid (wt. %) | Viscosity (mPa·s) at 52 $s^{-1}$ and 20° C. | Friction factor (tribology) (—) | | Sensory score (average of intensity of creaminess) |
|---|---|---|---|---|---|
| | | | 2.03 mm/s sliding speed | 20.3 mm/s sliding speed | |
| 5 | 10.8% maltodextrin | 28 | 0.581 | 0.102 | 5 |
| | 0.140% xanthan | 28 | 1.055 | 0.440 | 2 |
| | 14.7% maltodextrin | 73 | 0.358 | 0.036 | 7 |
| | 0.312% xanthan | 71 | 1.060 | 0.455 | 3 |
| 20 | 5.6% maltodextrin | 25 | 0.582 | 0.058 | 6 |
| | 0.045% xanthan | 19 | 1.019 | 0.292 | 2.5 |
| | 8.8% maltodextrin | 67 | 0.343 | 0.022 | 7 |
| | 0.195% xanthan | 81 | 0.824 | 0.232 | 3.5 |

Figure 24:
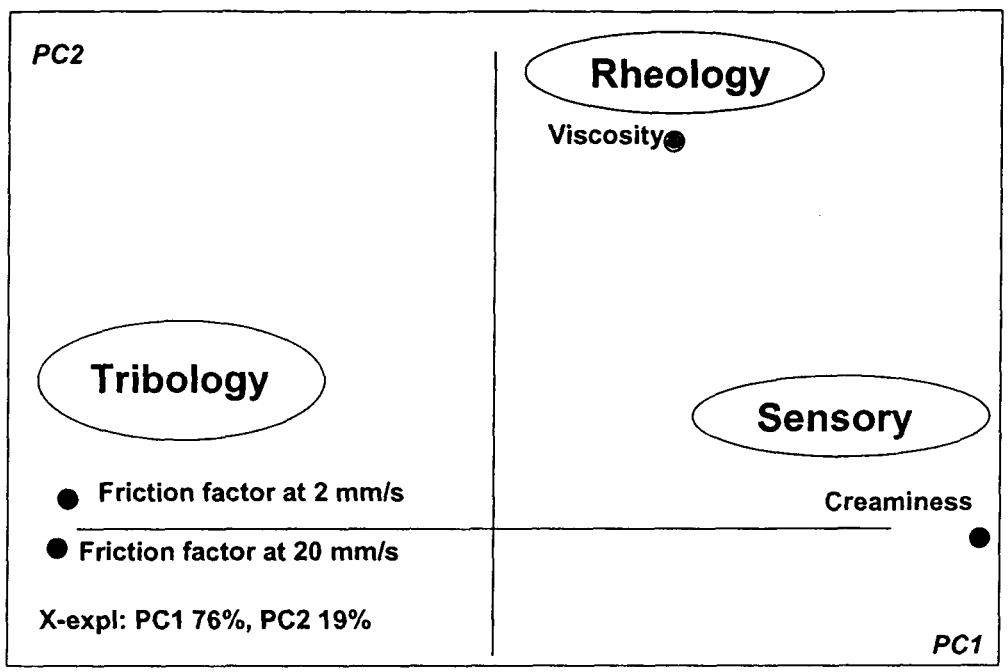
FIG. 24 is a PCA loading plot from the first two principal components PC1 and PC2.

The sensory score increase when the apparent viscosity of the emulsion is raised from ~20 to ~70 mPa·s. This is in agreement with the results of Akhtar et al. (2005). However, the PCA of the data tabulated above (see FIG. 24) show that the perceived creaminess is more sensitive to the friction factor than the apparent viscosity. In particular, with a background of identical droplet size distribution, fat content and apparent viscosity (at 52 $s^{-1}$), the 1DE maltodextrin is far more efficient than xanthan in reducing the friction factor.

Dickinson et al. (2006) found that iso-viscous emulsions (of identical fat content and droplet size distribution) gives a better score with maltodextrin than xanthan. They suggest that non-rheological factors may enhance the perception of creaminess. In particular, when panelists were asked to score stickiness (or mouth-coating), maltodextrin give a significantly better score than xanthan. This work shows that beyond rheology, friction factor clearly explain the differences in the perception of creaminess.

Example 9

Improvement of Mouthfeel of Milk

Figure 25:
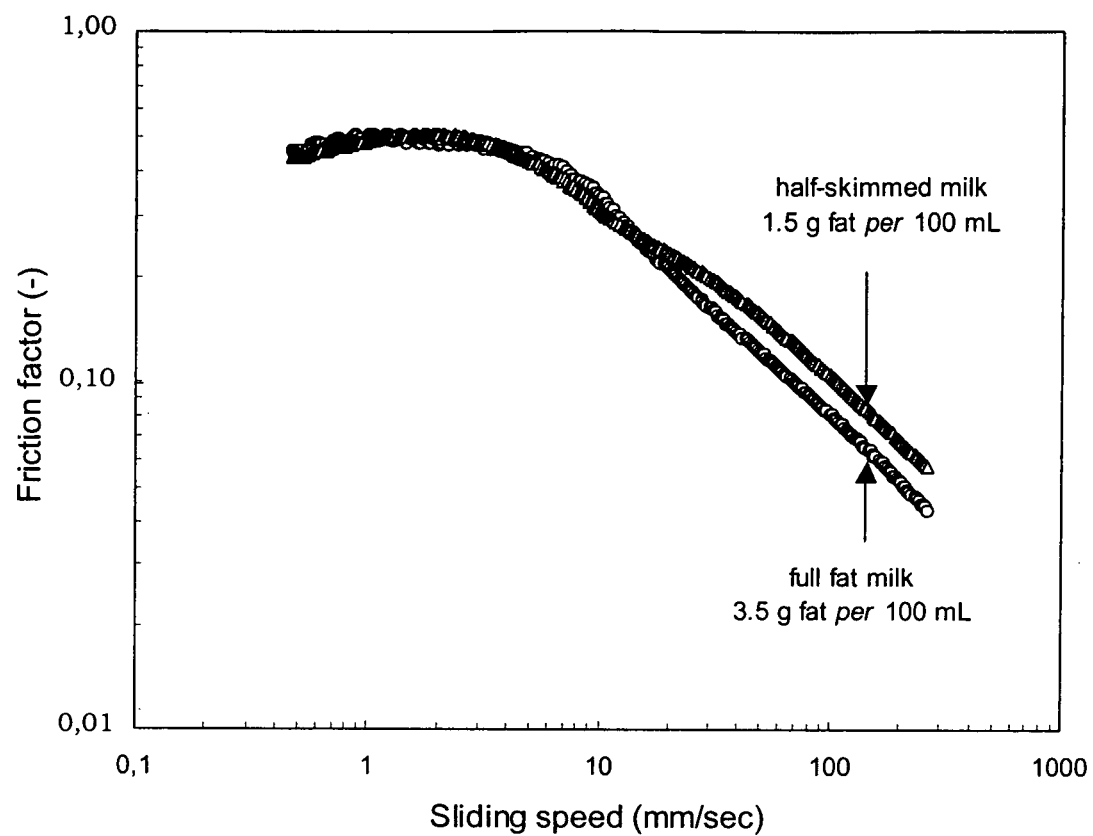
FIG. 25 is a graph showing the Stribeck curves of half-skimmed milk and full fat milk.
Figure 26:
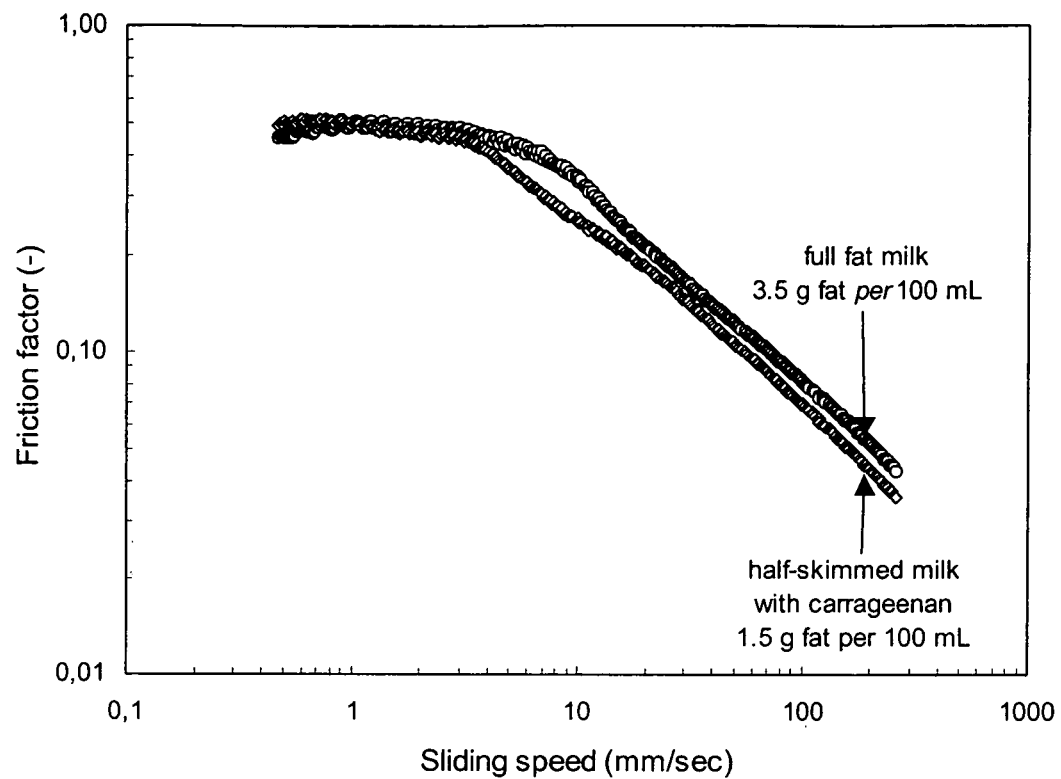
FIG. 26 is a graph showing the Stribeck curves of half-skimmed milk supplemented with carrageenan and full fat milk.

This example illustrates an embodiment of the method of the present invention for identifying a composition, selected from foods, food ingredients, ingredient blends or systems of ingredients, which is able to provide and/or improve mouthfeel sensations to a given food which lacks in these sensations:
a) obtain the tribological profile of full fat milk (3.5 g fat per 100 ml) having the desired mouthfeel;
b) obtain the tribological profile of half-skimmed milk (1.5 g fat per 100 ml) inferior in mouthfeel to full fat milk;
c) compare tribological profiles of full fat and half-skimmed milk (see FIG. 25);
d) identify an ingredient (i.e. carragheenan) that imparts a better mouthfeel (assessed by sensorial analysis; see Table 7) and a better tribological profile (see FIG. 26) when added to half-skimmed milk.

TABLE 7

| Property/attribute | Milk sample[1] | | |
|---|---|---|---|
| | Fresh whole milk | Fresh semi milk with carrageenan stabiliser | Fresh semi skimmed milk |
| Caloric content | | | |
| kJ/100 ml | 270 | 203 | 198 |
| kcal/100 ml | 64 | 48 | 47 |
| Protein (g/100 ml) | 3.5 | 3.5 | 3.5 |
| Carbohydrates (g/100 ml) | 4.5 | 5.0 | 4.5 |
| Fat (g/100 ml) | 3.5 | 1.5 | 1.5 |
| Sodium (g/100 ml) | 0.05 | 0.05 | 0.05 |
| Calcium (mg/100 ml) | 120 | 200 | 130 |
| Viscosity ($\eta$) (mPa · s) at | | | |
| 50 $s^{-1}$ and 4° C. | 4.7 | 14.9 | 3.8 |
| 50 $s^{-1}$ and 20° C. | 2.5 | 8.4 | 2.2 |
| Friction factor $\mu$ (—) at 20° C. and sliding speed of | | | |
| 50 mm/s | 0.122 | 0.106 | 0.157 |
| 100 mm/s | 0.081 | 0.069 | 0.106 |
| 250 mm/s | 0.045 | 0.037 | 0.060 |
| Sensory score (1 = poor mouthfeel (watery, thin); 10 = rich mouthfeel) | 5.1 | 7.5 | 4.0 |

[1]Friesche Vlag of Friesland Foods

Example 10

Improvement of Mouthfeel of Carbonated Soft Drinks

This example illustrates an embodiment of the method of the present invention for identifying a composition, selected from foods, food ingredients, ingredient blends or systems of ingredients, which is able to provide and/or improve mouthfeel sensations to a given food which lacks in these sensations:
a) obtain the tribological profile of full bodied carbonated soft drink sweetened with sucrose (10 wt. % sucrose) having the desired mouthfeel;
b) obtain the tribological profile of diet carbonated soft drink (sweetened with a HIS) inferior in mouthfeel to full bodied soft drink;
c) compare tribological profiles of full bodied and diet soft drink;
d) identify an ingredient (i.e. 0.037 wt. % Sunfiber and 8 wt. % trehalose) that imparts a better mouthfeel (assessed by sensorial analysis) and a better tribological profile (not shown) when added to HIS sweetened carbonated soft drink.

The invention claimed is:

1. A method for differentiating foods with respect to mouthfeel, comprising:
a) recording a first tribological profile by measuring the friction factor of a first food as a function of sliding speed using a tribology device;
b) recording a second tribological profile by measuring the friction factor of a second food as a function of sliding speed using said tribology device;
c) comparing said first tribological profile with said second tribological profile,
wherein said tribology device is a tribology device for assessing mouthfeel-related properties of a food sample, said tribology device comprising a motor and a measuring system comprising a first measuring element having at least a first measuring surface, and at least a second measuring element separated from said first measuring element and having at least one second measuring surface, at least one of said measuring elements being connected to said motor, said at least one first measuring surface and said at least one second measuring surface defining at least one contact measuring surface in which said food sample, during measurement, is disposed and sheared, wherein the width of the at least one contact measuring surface is adjustable by displacing said first measuring element and said at least one second measuring element relative to each other, and wherein at least one second measuring surface and/or at least one first measuring surface is composed of a thermoplastic elastomer having a delta friction factor of more than 0.2 between an aqueous 10% (w/w) sucrose solution and sunflower oil.

2. The method according to claim 1, wherein said tribology device comprises a motor-driven shaft and a measuring system consisting of an upper measuring element connected to said motor-driven shaft and having a first measuring surface, and a lower measuring element located at a separation below said upper measuring element and having at least one second measuring surface, said first measuring surface and each of said at least one second measuring surfaces defining a contact measuring surface in which said food sample, during measurement, is disposed and sheared, wherein the width of said contact measuring surface is adjustable by displacing said upper measuring element and said lower measuring element relative to each other, wherein said at least one second measuring surface and/or said first measuring surface is composed of a thermoplastic elastomer having a delta friction factor of more than 0.2 between an aqueous 10% (w/w) sucrose solution and sunflower oil.

3. The method according to claim 1, wherein said thermoplastic elastomer of said tribology device has a delta friction factor of more than 0.4 between an aqueous 10% (w/w) sucrose solution and sunflower oil.

4. The method according to claim 1, wherein said thermoplastic elastomer of said tribology device has a Shore A hardness of 25 to 75 or a tear strength of 2 to 12 N/mm.sup.2 or an elongation at break of 500 to 900% or a tear propagation at break of 2 to 35 N/mm.

5. The method according to claim 1, wherein said thermoplastic elastomer of said tribology device is a hydrogenated styrene block copolymer.

6. The method according to claim 1, wherein said first or upper measuring element of said tribology device is ball-shaped or is an at least partially spherical body.

7. The method according to claim 1, wherein said second or lower measuring element of said tribology device includes a support member and one or more substrates composed of said thermoplastic elastomer, wherein said one or more substrates are supported by said support member and each substrate provides a second measuring surface.

8. The method according to claim 7 wherein said one or more substrates of said tribology device are present in the form of plates or strips.

9. The method according to claim 8, wherein said plates or strips of said tribology device are releasably fastened to said support member via grooves formed in the surface of said support member facing said first or upper measuring element.

10. The method according to claim 8, wherein said second or lower measuring element of said tribology device exhibits three plates or strips.

11. The method according to claim 1, wherein said tribology device is a rheometer comprising said tribology device.

12. The method according to claim 1, wherein said measurement of friction factors is performed at a constant load of 1 to 10 N and/or at a temperature of 15° C. to 45° C. and/or at sliding speeds in the range of 0.4 to 250 mm/s.

13. A method for identifying a composition, selected from foods, food ingredients, ingredient blends or systems of ingredients, said composition being able to provide mouthfeel sensations to a given food and/or improve mouthfeel sensations of a given food which lacks in these sensations, comprising:
  a) obtaining a first target tribology profile by measuring the friction factor of a first food having desirable mouthfeel sensations as a function of sliding speed using a tribology device, wherein the tribology device is a tribology device for assessing mouthfeel-related properties of a food sample, said tribology device comprising a motor and a measuring system comprising a first measuring element having at least a first measuring surface, and at least a second measuring element separated from said first measuring element and having at least one second measuring surface, at least one of said measuring elements being connected to said motor, said at least one first measuring surface and said at least one second measuring surface defining at least one contact measuring surface in which said food sample, during measurement, is disposed and sheared, wherein the width of the at least one contact measuring surface is adjustable by displacing said first measuring element and said at least one second measuring element relative to each other, and wherein at least one second measuring surface and/or at least one first measuring surface is composed of a thermoplastic elastomer having a delta friction factor of more than 0.2 between an aqueous 10% (w/w) sucrose solution and sunflower oil;
  b) obtaining a second tribology profile by measuring the friction factor of a second food using a tribology device, said second food being a mixture of said given food, which lacks and/or is inferior in one or more of the desirable mouthfeel sensations of said first food, and said composition to be identified;
  c) comparing said first target tribology profile with said second tribology profile; and
  d) identifying said composition being able to provide mouthfeel sensations to said given food lacking in these sensations, which results in a second tribology profile that is substantially equivalent to said first target tribology profile.

14. A method for predicting sensory mouthfeel attributes of a food, comprising:
  a) obtaining a tribology data set by measuring the friction factor of a food as a function of sliding speed using a tribology device, wherein the tribology device is a tribology device for assessing mouthfeel-related properties of a food sample, said tribology device comprising a motor and a measuring system comprising a first measuring element having at least a first measuring surface, and at least a second measuring element separated from said first measuring element and having at least one second measuring surface, at least one of said measuring elements being connected to said motor, said at least one first measuring surface and said at least one second measuring surface defining at least one contact measuring surface in which said food sample, during measurement, is disposed and sheared, wherein the width of the at least one contact measuring surface is adjustable by displacing said first measuring element and said at least one second measuring element relative to each other, and wherein at least one second measuring surface and/or at least one first measuring surface is composed of a thermoplastic elastomer having a delta friction factor of more than 0.2 between an aqueous 10% (w/w) sucrose solution and sunflower oil; and
  b) determining one or more sensory mouthfeel attributes of said food, based on a predetermined correlation model, wherein said correlation model is established by
  b1) defining one or more sensory mouthfeel attributes of a reference food by a sensory analysis;
  b2) collecting a sensory data set by sensorially scoring said reference food in terms of said one or more sensory mouthfeel attributes defined in step b1);
  b3) collecting a tribology data set by measuring the friction factor of said reference food as a function of sliding speed using the tribology device;
  b4) building up a correlation model between said tribological data set obtained in step b3) and said sensory data set obtained in step b2) to predict said one or more sensory mouthfeel attributes.

* * * * *